US010314305B2

(12) United States Patent
Schneider et al.

(10) Patent No.: US 10,314,305 B2
(45) Date of Patent: Jun. 11, 2019

(54) LIQUID AGROCHEMICAL COMPOSITIONS COMPRISING A POLYMERIC THICKENER AND AN ALCOHOL-CONTAINING SOLVENT SYSTEM, AND LIQUID HERBICIDAL COMPOSITIONS HAVING AN ALCOHOL-CONTAINING SOLVENT SYSTEM

(71) Applicant: Syngenta Participations AG, Basel (CH)

(72) Inventors: Rudolf Schneider, Muenchwilen (CH); Phillippe Blind, Muenchwilen (CH)

(73) Assignee: SYNGENTA PARTICIPATIONS AG, Basel (CH)

( * ) Notice: Subject to any disclaimer, the term of this patent is extended or adjusted under 35 U.S.C. 154(b) by 0 days.

(21) Appl. No.: 14/436,495

(22) PCT Filed: Oct. 17, 2013

(86) PCT No.: PCT/EP2013/071796
§ 371 (c)(1),
(2) Date: Apr. 17, 2015

(87) PCT Pub. No.: WO2014/060557
PCT Pub. Date: Apr. 24, 2014

(65) Prior Publication Data
US 2015/0264923 A1    Sep. 24, 2015

(30) Foreign Application Priority Data

Oct. 19, 2012  (GB) .................................. 1218973.4
Nov. 8, 2012   (GB) .................................. 1220176.0

(51) Int. Cl.
*A01N 25/32*    (2006.01)
*A01N 43/90*    (2006.01)
(Continued)

(52) U.S. Cl.
CPC .............. *A01N 25/32* (2013.01); *A01N 25/02* (2013.01); *A01N 43/40* (2013.01); *A01N 43/42* (2013.01); *A01N 43/90* (2013.01)

(58) Field of Classification Search
CPC ........ A01N 25/32; A01N 25/02; A01N 43/40; A01N 43/42; A01N 43/90
See application file for complete search history.

(56) References Cited

U.S. PATENT DOCUMENTS 6,146,652 A * 11/2000 Gore ....................... A01N 25/22
424/405
6,426,082 B1    7/2002 Ueda et al.
6,451,731 B1    9/2002 Agbaje et al.
2008/0311221 A1  12/2008 Sanson et al.
2009/0005246 A1 *  1/2009 Schneider ............... A01N 43/90
504/108
(Continued)

FOREIGN PATENT DOCUMENTS

DE    10258216 A1    7/2004
EP     1886560 A1    2/2008
(Continued)

OTHER PUBLICATIONS

Database WPI Week 200543 Thomson Scientific, London, GB; AN 2005-421629, Jun. 16, 2005.
(Continued)

*Primary Examiner* — Johann R Richter
*Assistant Examiner* — Genevieve S Alley
(74) *Attorney, Agent, or Firm* — BakerHostetler; Toni-Junell Herbert

(57) ABSTRACT

The invention provides a liquid agrochemical composition, preferably in the form of an emulsifiable concentrate (EC), comprising a mixture of: one or more agrochemically active ingredients (in particular comprising one or more herbicides); a $C_1$-$C_6$ alkyl methacrylate polymer (preferably an isobutyl methacrylate polymer); and a solvent system comprising: (c1) an alcohol solvent comprising hexylene glycol (2-methyl-2,4-pentanediol), benzyl alcohol, diacetone alcohol (2-methyl-4-oxo-pentane-2-ol), isobutanol, n-pentanol, n-hexanol, n-heptanol, n-octanol, 2-ethyl-hexanol, cyclohexanol, dipropylene glycol, diethylene glycol monomethyl ether, dipropylene glycol monomethyl ether, ethylene glycol, or a mixture of two or more of these alcohols (preferably hexylene glycol); and (c2) a heavy aromatic hydrocarbon solvent. The $C_1$-$C_6$ alkyl methacrylate polymer generally acts as a thickener which is suitable for the defined solvent system, and which is for increasing the viscosity of the composition. The invention also provides a liquid herbicidal composition, preferably in the form of an emulsifiable concentrate, comprising a mixture of: (a) one or more agrochemically active ingredients comprising one or more herbicides, wherein the one or more herbicides comprise: (a1) pinoxaden; (a2) florasulam or a salt; (a2a) metosulamor a salt; (a2b) diclosulam or a salt; (a2c) cloransulam-methyl; or (a3) clodinafop-propargyl; or a combination of either (a2) florasulam or (a2a) metosulamor a salt of one of these with (a1) pinoxaden and/or (a3) clodinafop-propargyl; and (c) a solvent system comprising: (c3) a ($C_2$-$C_6$-alkylene) carbonate such as 1,2-propylene carbonate; and (c1a) an alcohol solvent comprising hexylene glycol, benzyl alcohol, diacetone alcohol, isobutanol, n-pentanol, n-hexanol, n-heptanol, n-octanol, 2-ethyl-hexanol, cyclohexanol, dipropylene glycol, diethylene glycol monomethyl ether, dipropylene glycol monomethyl ether, or a mixture of two or more of these alcohols (preferably benzyl alcohol).

7 Claims, No Drawings

(51) Int. Cl.
*A01N 43/40* (2006.01)
*A01N 25/02* (2006.01)
*A01N 43/42* (2006.01)

(56) References Cited

U.S. PATENT DOCUMENTS

2011/0098178 A1* 4/2011 Stock .................... A01N 43/40
 504/103
2011/0275516 A1 11/2011 Wu et al.

FOREIGN PATENT DOCUMENTS

| | | |
|---|---|---|
| EP | 2305030 A1 | 4/2011 |
| GB | 2003904 A | 3/1979 |
| GB | 2048675 A | 12/1980 |
| JP | 2005/154344 A | 6/2005 |
| WO | 91/04969 A1 | 4/1991 |
| WO | 95/007613 A1 | 3/1995 |
| WO | 2002/45507 A2 | 6/2002 |
| WO | 2007/073933 A2 | 7/2007 |
| WO | 2008/049618 A2 | 5/2008 |
| WO | 2011/023758 A2 | 3/2011 |

OTHER PUBLICATIONS

"Poly isobutyl methacrylate", Jan. 1, 1994 (Jan. 1, 1994), pp. 1-1, XP055087872, Retrieved from the Internet: URL:http://www.biopolymersource.com/dataSheet/P8467-iBuMA.pdf.
International Search Report for PCT/EP2013/071796 dated Dec. 17, 2013.
UK Search Report for GB1220176.0, claims 14-17 & 26 dated Jun. 26, 2013.
UK Search Report for GB1220176.0, claims 18-25 & 26 dated Jun. 26, 2013.
UK Search Report for GB1220176.0, claims 27-30 dated Jun. 26, 2013.
UK Search Report for GB1220176.0, claims 1-13 & 26 dated Mar. 11, 2013.

* cited by examiner

LIQUID AGROCHEMICAL COMPOSITIONS COMPRISING A POLYMERIC THICKENER AND AN ALCOHOL-CONTAINING SOLVENT SYSTEM, AND LIQUID HERBICIDAL COMPOSITIONS HAVING AN ALCOHOL-CONTAINING SOLVENT SYSTEM

RELATED APPLICATION INFORMATION

This application is a 371 of International Application No. PCT/EP2013/071796, filed 17 Oct. 2013, which claims priority to GB Patent Application No. 1218973.4 filed 19 Oct. 2012; and GB Patent Application No. 1220176.0 filed 8 November 2012, the contents of which are incorporated herein by reference herein.

The present invention relates to a liquid agrochemical (preferably herbicidal) composition, in particular in the form of an emulsifiable concentrate (EC), and/or in particular comprising inter alia pinoxaden. The present invention also relates to methods for controlling and/or inhibiting the growth of weeds, such as monocotyledonous and/or dicotyledonous weeds, comprising applying to the weeds or to their locus a liquid agrochemical composition (which is herbicidal) (e.g. an EC), in particular comprising inter alia pinoxaden.

EP 0 875 143 B1 (assigned to Dow) discloses a homogeneous blend of 0.01-40% by weight of certain oil-soluble polymers and one or more pesticides soluble in the polymer or in its monomers or in a solution of the polymer in an organic solvent. The monomer units from the polymer can be 1 or more of substituted or unsubstituted alkyl acrylates, alkyl methacrylates, acrylamides or methacrylamides.

US 2011/0237439 A1 (Tuerk et al., assignee BASF SE) discloses a process for the preparation of random radical copolymers, using a defined olefinically unsaturated sulfonic acid and at least 2 structurally different defined olefinically unsaturated monomers; and agrochemical compositions comprising the produced random radical copolymers.

US 2007/0004851 A1 (F. Zeng, Rohm and Haas) discloses a polymeric thickener for aqueous systems.

US 2008/0311221 A1 (Sanson, assignee PBI/Gordon Corp.) discloses a Lewis acid and oil-soluble hybrid pesticide concentrate that spontaneously forms a water-based microemulsion. Propylene carbonate is a preferred solvent for use therein.

Pinoxaden is a herbicide suitable for use on non-oat cereals such as wheat, barley, rye and/or triticale, especially wheat and/or barley, and is typically applied post-emergence for control of grassy weeds such as those from the genus *Alopecurus, Apera, Avena, Lolium, Phalaris* or *Setaria*, e.g. at application rates of from 30 to 60 g of pinoxaden/ha (ha=hectare); pinoxaden is typically and preferably used in admixture with cloquintocet-mexyl as a safener (these features, e.g. uses and/or application rates and/or safener can be used in the present invention). Emulsifiable concentrate (EC) formulations of pinoxaden are available from Syngenta in many countries, typically under the trade mark Axial™; e.g. in the USA it is available under the trade mark Axial™ and Axial XL™. Pinoxaden is disclosed as Example H9 and as Compound no. 1.008 in WO 99/47525 A1 (Novartis AG). Pinoxaden and its herbicidal uses are disclosed in: M. Muehlebach et al., *Bioorganic & Medicinal Chemistry*, 2009, vol. 17, pp. 4241-4256; M. Muehlebach et al., in "*Pesticide Chemistry. Crop Protection, Public Health, Environmental Safety*", ed. H. Ohkawa et al., 2007, Wiley, Weinheim, pp. 101-110; U. Hofer et al. *Journal of Plant Diseases and Protection*, 2006, Special Issue XX, pp. 989-995; and "*The Pesticide Manual*", ed. C. D. S. Tomlin, 15th edition, 2009, British Crop Production Council, UK, see entry 687 "pinoxaden" on pp. 911-912. Pinoxaden is 8-(2,6-diethyl-4-methylphenyl)-1,2,4,5-tetrahydro-7-oxo-7H-pyrazolo[1,2-d][1,4,5]oxadiazepin-9-yl 2,2-dimethylpropionate and has the following structure:

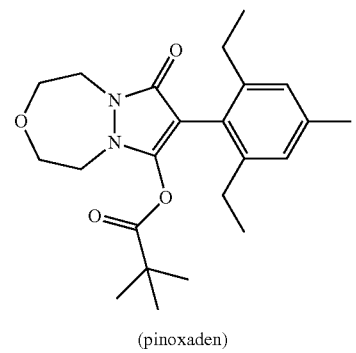 [SMILES: CCc1cc(C)cc(CC)c1-c1c(OC(=O)C(C)(C)C)n2n(c1=O)CCOCC2]

(pinoxaden)

WO 01/17351 A1 (Syngenta Participations AG) discloses herbicidal compositions comprising (a) a genus of herbicidal fused 3-hydroxy-4-(4-methylphenyl)-5-oxo-pyrazoline derivatives encompassing, and exemplifying, pinoxaden; and (b) a co-herbicide selected the classes of phenoxy-phenoxypropionic acids (e.g. clodinafop-propargyl, diclofop-methyl, fluazifop-P-butyl, fenoxaprop-P-ethyl, et al.), hydroxylamines (e.g. tralkoxydim, et al.), sulfonylureas (e.g. triasulfuron, et al.), imidazolinones, pyrimidines, triazines, ureas, PPO, chloroacetanilides, phenoxyacetic acids, triazinones, dinitroanilines, azinones, carbamates, oxyacetamides, thiolcarbamates, azole-ureas, benzoic acids, anilides, nitriles, triones and sulfonamides (e.g. diclosulam, florasulam, flumetsulam, metosulam, et al.), as well as from the herbicides amitrol, benfuresate, bentazone, cinmethylin, clomazone, chlopyralid, difenzoquat, dithiopyr, ethofumesate, flurochloridone, indanofane, isoxaben, oxaziclomefone, pyridate, pyridafol, quinchlorac, quinmerac, tridiphane and flamprop. Pages 10-11 of WO 01/17351 A1 disclose a long list of possible co-herbicides which can be used.

WO 2007/073933 A2 (Syngenta Participations AG) discloses emulsifiable concentrates containing, in addition to emulsifiers and water-insoluble solvents, a) pinoxaden and b) an alcohol, preferably benzyl alcohol, tetrahydrofurfuryl alcohol or 2-methyl-2,4-pentanediol.

Copending patent application PCT/EP2012/056766, filed on 13 Apr. 2012 and published on 15 Nov. 2012 as WO 2012/152527 A2 (Syngenta Participations AG), discloses an liquid emulsifiable concentrate composition comprising a mixture of: pinoxaden, a $C_1$-$C_{12}$alkyl ester or a 2-($C_1$-$C_6$alkoxy)$C_2$-$C_4$alkyl-ester of fluroxypyr, and a built-in phosphate and/or phosphonate adjuvant; wherein the built-in phosphate and/or phosphonate adjuvant comprises a tris-[$C_4$-$C_{12}$alkyl or 2-($C_2$-$C_6$alkoxy)$C_2$-$C_4$alkyl-]ester of phosphoric acid (preferably tris-(2-ethylhexyl)phosphate) and/or a bis-($C_3$-$C_{12}$alkyl) ester of a $C_3$-$C_{12}$alkyl-phosphonic acid. In WO 2012/152527 A2, most preferably, the ester of fluroxypyr is the 1-methylheptyl ester of fluroxypyr, also named fluroxypyr-meptyl. WO 2012/152527 A2 also discloses methods for controlling and/or inhibiting the growth of *dicotyledonous and/or broadleaf weeds*, such as weeds from the genus *Kochia, Polygonum, Fallopia, Salsola, Des-*

*curainia, Helianthus, Lactuca, Sinapsis* and/or *Amaranthus*, e.g. using the emulsifiable concentrate composition.

WO 2008/049618 A2 (Syngenta Participations AG) discloses a liquid herbicidal composition containing pinoxaden and an adjuvant, where the adjuvant is a built-in adjuvant consisting of a tris-ester of phosphoric acid with aliphatic or aromatic alcohols and/or a bis-ester of alkyl phosphonic acids with aliphatic or aromatic alcohols. WO 2008/049618 discloses the following preferred built-in adjuvants: the tris-ester of phosphoric acid is preferably tris-(2-ethylhexyl) phosphate, tris-n-octyl phosphate or tris-butoxyethyl phosphate; and the bis-ester of alkyl phosphonic acids is preferably bis-(2-ethylhexyl)-(2-ethylhexyl)-phosphonate, bis-(2-ethylhexyl)-(n-octyl)-phosphonate, dibutyl-butyl phosphonate or bis(2-ethylhexyl)-tripropylene-phosphonate. WO 2008/049618 (e.g. pages 7-9 thereof) discloses that Example 1 Compositions A and B therein—which are emulsifiable concentrate (EC) compositions containing 5% or 6.9% w/v pinoxaden (as the herbicide), 1.25% or 1.725% w/v cloquintocet-mexyl (as a safener), 5% w/v castor oil ethoxylate (30 EO) and 2% w/v calcium alkylbenzene sulfonate (as two emulsifiers), 34% or 32% w/v tris-(2-ethylhexyl)phosphate (as the built-in adjuvant), 18% w/v tetrahydrofurfuryl alcohol (as a first solvent), and the remainder as a mixture of aromatic hydrocarbons (as a second solvent)—showed an enhanced chemical stability of pinoxaden, in comparison to other pinoxaden EC formulations containing different built-in adjuvants. The good herbicidal efficacy of the pinoxaden on the grassy weeds from the genera *Alopecurus, Apera, Avena, Lolium*, and *Phalaris* was also maintained (see WO 2008/049618, Example 3, pages 10-11). WO 2008/049618 discloses on page 6 that the weeds to be controlled may be both monocotyledonous and dicotyledonous weeds, such as, for example, *Stellaria, Apera, Avena, Setaria, Sinapis, Lolium, Echinochloa, Bromus, Alopecurus, Phalaris, Amaranthus, Chenopodium, Convolvulus, Chrysanthemum, Papaver, Cirsium, Polygonum, Matricaria, Galium, Viola* and *Veronica*. WO 2008/049618 discloses on page 5 that a further co-herbicide in addition to pinoxaden can optionally be incorporated into the composition.

In the pinoxaden compositions disclosed in WO 2008/049618 Example 1 Compositions A and B (pages 7-9 therein), the mixture of aromatic solvents used is typically a mixture of heavy aromatic hydrocarbons (see WO 2008/049618 page 4 paragraph 3), for example Solvesso™ such as Solvesso™ 200 ND.

Heavy aromatic solvents such as Solvesso™, usually containing inter alia $C_1$-$C_4$alkyl-naphthalenes, have the potential to cause human lung damage following oral ingestion, if part of the solvents pass down the human trachea (i.e. there is a potential aspiration hazard). Therefore, a liquid agrochemical (e.g. EC) composition containing heavy aromatic solvents has the potential that some of the solvent therein might reach and possibly damage the human lungs after accidental oral ingestion of the liquid (e.g. EC) composition by a user such as a farmer. Therefore, it can be preferable to use a thickener in the liquid agrochemical (e.g. EC) composition—preferably, the thickener is dissolved in the heavy aromatic solvents. The thickener increases the viscosity of the liquid agrochemical (e.g. EC) composition, reducing the potential for entry to the human lungs and any potential damage caused therein, after accidental oral ingestion.

It is also possible, though it is not confirmed, that the use of a dissolved thickener in the heavy aromatic solvents, such as Solvesso™, might somewhat reduce human skin penetration of the solvents and/or of a liquid agrochemical composition containing such solvents, e.g. after accidental spillage by a user onto the skin, for example in the event that a significant amount of unsubstituted naphthalene (which is a good skin penetration agent) is present in the heavy aromatic solvents (which is not preferred).

For the pinoxaden compositions disclosed in WO 2008/049618 Example 1 Compositions A and B (pages 7-9 therein) containing tetrahydrofurfuryl alcohol as the first solvent, when a mixture of heavy aromatic hydrocarbons such as Solvesso™ 200 ND is chosen as the second (aromatic) solvent, a suitable thickener (e.g. for use in Europe) has been found to be polystyrene, typically present at about 0.5% w/v of the pinoxaden EC and/or present as STYRON 666D CLEAR™ (see e.g. Reference Formulation Example 14 hereinafter). This works well because polystyrene, in the relevant concentrations, is soluble in typical mixtures of tetrahydrofurfuryl alcohol+heavy aromatic hydrocarbons.

In certain countries such as European Union countries, it is now thought to be preferred to replace the tetrahydrofurfuryl alcohol ("THFA") solvent used in known pinoxaden EC compositions (e.g. as disclosed in WO 2007/073933 or WO 2008/049618) with a different solvent, or to reduce the amount of THFA, for environmental, regulatory and/or other related reasons.

However, it has been found that when the alcoholic solvent in the pinoxaden EC composition is changed from tetrahydrofurfuryl alcohol to hexylene glycol (2-methyl-2,4-pentanediol), the polystyrene thickener is not sufficiently soluble at relevant concentrations in typical mixtures of hexylene glycol+heavy aromatic hydrocarbons. The polystyrene dissolves in the mixture of heavy aromatic hydrocarbons, but when the hexylene glycol is added the polystyrene generally precipitates out of solution, usually to form a sticky insoluble mass which may block pipes and filters. This makes polystyrene less useful and not very suitable as a thickener in EC compositions containing a mixture of hexylene glycol+heavy aromatic hydrocarbons.

A large number of alternative substances were tested as potential thickeners, but almost all of them were found not to be suitable as thickeners for a solvent system comprising hexylene glycol and heavy aromatic hydrocarbon mixtures, usually because, like polystyrene, they were insufficiently soluble in this particular solvent system, with the solubility in the hexylene glycol component of the solvent system being thought to be the main problem.

Finally, after much testing, it has been found that a thickener comprising a polymer of isobutyl methacrylate is soluble in, and so is a suitable thickener for, a solvent system comprising: (i) hexylene glycol and (ii) heavy aromatic hydrocarbon mixtures (specifically, Solvesso™). This discovery has enabled a suitable pinoxaden EC composition containing this solvent system and this thickener to be made which is herbicidally efficacious against grassy weeds sensitive to pinoxaden, and which suitable for commercialization in countries where the presence of the thickener in heavy-aromatic-hydrocarbon-containing agrochemical compositions is desirable or mandated.

The combination of (a) the solvent system comprising hexylene glycol (2-methyl-2,4-pentanediol) and heavy aromatic hydrocarbon mixtures and (b) the poly(isobutyl methacrylate) thickener is also thought to be generally useful in liquid agrochemical compositions (in particular emulsifiable concentrates), independent of which agrochemically active ingredient(s) is or are present in the composition.

Further, the poly(isobutyl methacrylate) thickener is also thought to be, or is likely to be, preferable to (i.e. more soluble than) polystyrene in solvent systems containing heavy aromatic hydrocarbon mixtures combined with other alcoholic organic solvents suitable for liquid compositions such as emulsifiable concentrates (e.g. pinoxaden-containing ECs), such as: benzyl alcohol, diacetone alcohol (2-methyl-4-oxo-pentane-2-ol, also named 4-hydroxy-4-methyl-2-pentanone), n-hexanol, n-octanol, 2-ethyl-hexanol, cyclohexanol, dipropylene glycol, diethylene glycol monomethyl ether, dipropylene glycol monomethyl ether, or ethylene glycol, or possibly other alcohols such as isobutanol, n-pentanol or n-heptanol.

It is also possible that a variety of alkyl (e.g. $C_1$-$C_6$ alkyl such as $C_3$-$C_5$ alkyl) methacrylate polymers might also be suitable thickeners for liquid agrochemical compositions, e.g. containing the above-mentioned solvent systems.

Therefore, according to a first aspect of the present invention, there is provided a liquid agrochemical (preferably herbicidal) composition, preferably in the form of an emulsifiable concentrate (EC), comprising a mixture of:
(a) one or more agrochemically active ingredients (preferably comprising one or more herbicides);
(b) a $C_1$-$C_6$ alkyl methacrylate polymer (preferably an isobutyl methacrylate polymer); and
(c) a solvent system comprising:
  (c1) an alcohol solvent comprising hexylene glycol (2-methyl-2,4-pentanediol), benzyl alcohol, diacetone alcohol (2-methyl-4-oxo-pentane-2-ol, or 4-hydroxy-4-methyl-2-pentanone), isobutanol, n-pentanol, n-hexanol, n-heptanol, n-octanol, 2-ethyl-hexanol, cyclohexanol, dipropylene glycol, diethylene glycol monomethyl ether, dipropylene glycol monomethyl ether, ethylene glycol, or a mixture of two or more of these alcohols; and
  (c2) a heavy aromatic hydrocarbon solvent.

Preferably, in the first aspect of the invention, the liquid agrochemical (e.g. herbicidal) composition, in particular in the form of an emulsifiable concentrate (EC), contains substantially no water (in particular less than 1% w/w of water, more particularly less than 0.5% w/w, e.g. equal to or less than 0.2% w/w, by weight of the liquid agrochemical (preferably herbicidal) composition).

Turning now to a further (second) aspect of the invention: Known agrochemical emulsifiable concentrate (EC) compositions often have at least 1 non-ionic surfactant/emulsifier and at least 1 ionic (e.g. anionic) surfactant/emulsifier. This is to maximize the chance of obtaining stable emulsion droplets after the EC is mixed with water, because the two different surfactant classes have different ways of stabilizing droplets. For example, the pinoxaden-containing EC compositions disclosed as Example 1 Compositions A and B and Example 2 Compositions G, H and I on pages 7-10 of WO 2008/049618 A2 contain 5% w/v castor oil ethoxylate (30EO), a non-ionic emulsifier, and 2% w/v of alkylbenzenesulfonate calcium salt, an anionic emulsifier. Similarly, Example 1 (EC1-3) and Examples 2, 3, 5 and 6 on pages 5-8 of WO 2007/073933 A2 disclose pinoxaden ECs with 1 or 2 nonionic emulsifiers and 1 anionic emulsifier.

However, in a further (second) aspect of the invention, a surfactant system comprising three specific non-ionic surfactants has now been discovered, which is believed to be a particularly suitable surfactant system for agrochemical liquid (e.g. emulsifiable concentrate, EC) compositons, and, in particular, which is a particularly suitable surfactant system for pinoxaden-containing EC compositions.

Therefore, according to the second aspect of the present invention, there is provided a liquid agrochemical (preferably herbicidal) composition, preferably in the form of an emulsifiable concentrate (EC), comprising a mixture of:
(a) one or more agrochemically active ingredients (preferably comprising one or more herbicides); and
(d) a surfactant system comprising (in particular consisting essentially of, e.g. being):
  (d1) a butanol [ethylene oxide (EO)-propylene oxide (PO)] copolymer;
  (d2) castor oil ethoxylate; and
  (d3) a block copolymer of ethylene oxide (EO) and propylene oxide (PO).

Preferably, in the second aspect of the invention, the liquid agrochemical (e.g. herbicidal) composition, in particular in the form of an emulsifiable concentrate (EC), contains substantially no water (in particular less than 1% w/w of water, more particularly less than 0.5% w/w, e.g. equal to or less than 0.2% w/w, by weight of the liquid agrochemical e.g. herbicidal composition).

In a preferable embodiment of the invention, the features of the first and second aspects of the invention are combined in a or the liquid agrochemical (e.g. herbicidal) composition.

A further (third) aspect of the invention has also been discovered in the context of removing tetrahydrofurfuryl alcohol ("THFA")) from pinoxaden and florasulam containing emulsifiable concentrates (ECs) such as Compositions G and I from page 10 of WO 2008/049618 A2. THFA is an excellent solvent for pinoxaden, florasulam and clodinafop-propargyl, and when removed from the EC it was found that two solvents are generally required to replace it in order to keep all active ingredients (e.g. pinoxaden, florasulam, and optionally clodinafop-propargyl) dissolved in the EC. In this third aspect of the invention, a new solvent system comprising an alkylene carbonate such as 1,2-propylene carbonate (combined with a defined alcohol solvent, most preferably benzyl alcohol) has been discovered, which is believed to be a particularly suitable solvent system for agrochemical (herbicidal) liquid (e.g. EC) compositions comprising pinoxaden, florasulam or an agrochemically acceptable salt thereof, or clodinafop-propargyl, or (more preferably) a combination of pinoxaden, and florasulam or an agrochemically acceptable salt thereof, and optionally clodinafop-propargyl. It has been found that 1,2-propylene carbonate is an excellent solvent for florasulam but only a moderately good solvent for pinoxaden. Benzyl alcohol is a excellent solvent for pinoxaden (up to about 55% w/w pinoxaden dissolves in benzyl alcohol at 20° C.) but benzyl alcohol is only a moderately good solvent for florasulam. Therefore, a combination of 1,2-propylene carbonate and benzyl alcohol (in practice also combined with a heavy aromatic hydrocarbon solvent such as Solvesso™) was used to solubilize both the pinoxaden and the florasulam fully and reliably in the EC. It is also thought likely that other agrochemically-acceptable alcohol solvents which are good solvents for pinoxaden should also work in this invention, in particular: hexylene glycol (2-methyl-2,4-pentanediol) (in which up to ca. 21.1% w/w pinoxaden dissolves at 20° C.), diacetone alcohol (2-methyl-4-oxo-pentane-2-ol, or 4-hydroxy-4-methyl-2-pentanone, in which up to ca. 27.5% w/w pinoxaden dissolves at 20° C.), isobutanol, n-pentanol, n-hexanol (in which up to ca. 25-30% w/w pinoxaden dissolves at 20° C.), n-heptanol, n-octanol (in which up to ca. 15.3% w/w pinoxaden dissolves at 20° C.), 2-ethyl-hexanol (in which up to ca. 18.7% w/w pinoxaden dissolves at 20° C.), cyclohexanol (in which up to ca. 19.8% w/w pinoxaden dissolves at 20° C.), dipropylene glycol (in which up to ca. 11.4% w/w pinoxaden dissolves at 20° C.), diethylene glycol monomethyl ether, or dipropylene glycol monomethyl ether, or a mixture of two or more alcohols selected from the previously-mentioned alcohols and benzyl alcohol.

In this third aspect of the invention, it was time-consuming and difficult to discover that the present alkylene carbonate and alcohol containing solvent system was a suitable solvent system (not requiring tetrahydrofurfuryl alcohol ("THFA")) for pinoxaden and florasulam or an agrochemically acceptable salt thereof, especially considering special and/or difficult considerations regarding solubilizing florasulam. Other agrochemically active ingredients e.g. herbicides might benefit as well from this new solvent system, in particular metosulam, diclosulam, or cloransulam-methyl, all of which are in the same triazolopyrimidine sulfonamide class of ALS inhibitor herbicides as florasulam, and which are thought likely to have somewhat similar or acceptably good solubilities in 1,2-propylene carbonate.

Therefore, according to the third aspect of the present invention, there is provided a liquid herbicidal composition, preferably in the form of an emulsifiable concentrate (EC), comprising a mixture of:

(a) one or more agrochemically active ingredients comprising (e.g. consisting essentially of or being) one or more herbicides, wherein the one or more herbicides comprise:
  (a1) pinoxaden;
  or (a2) florasulam or an agrochemically acceptable salt thereof;
  or (a2a) metosulam or an agrochemically acceptable salt thereof;
  or (a2b) diclosulam or an agrochemically acceptable salt thereof;
  or (a2c) cloransulam-methyl;
  or (a3) clodinafop-propargyl;
  or a combination of (a2) florasulam or an agrochemically acceptable salt thereof with (a1) pinoxaden and/or (a3) clodinafop-propargyl;
  or a combination of (a2a) metosulam or an agrochemically acceptable salt thereof with (a1)) pinoxaden and/or (a3) clodinafop-propargyl;
  and
(c) a solvent system comprising:
  (c3) a $(C_2$-$C_6$-alkylene) carbonate; and
  (c1a) an alcohol solvent comprising (e.g. consisting essentially of or being) hexylene glycol (2-methyl-2,4-pentanediol), benzyl alcohol, diacetone alcohol (2-methyl-4-oxo-pentane-2-ol, or 4-hydroxy-4-methyl-2-pentanone), isobutanol, n-pentanol, n-hexanol, n-heptanol, n-octanol, 2-ethyl-hexanol, cyclohexanol, dipropylene glycol, diethylene glycol monomethyl ether, dipropylene glycol monomethyl ether, or a mixture of two or more of these alcohols.

In the third aspect of the invention, preferably, the florasulam or the salt thereof is florasulam, and/or the metosulam or the salt thereof is metosulam, and/or the diclosulam or the salt thereof is diclosulam.

In the third aspect of the invention, it is particularly preferred that the one or more agrochemically active ingredients (a) comprise (e.g. consist essentially of or are) one or more herbicides, wherein the one or more herbicides comprise:
  (a1) pinoxaden; or (a2) florasulam or an agrochemically acceptable salt thereof; or (a3) clodinafop-propargyl; or a combination of (a2) florasulam or an agrochemically acceptable salt thereof with (a1) pinoxaden and/or (a3) clodinafop-propargyl. In this embodiment, preferably, the florasulam or the salt thereof is florasulam.

In the third aspect of the invention, it is even more particularly preferred that the one or more agrochemically active ingredients (a) comprise (e.g. consist essentially of or are) one or more herbicides, wherein the one or more herbicides comprise:
  (a1) pinoxaden; or (a2) florasulam or an agrochemically acceptable salt thereof; or a combination of: (a1) pinoxaden, with (a2) florasulam or an agrochemically acceptable salt thereof, and optionally also with (a3) clodinafop-propargyl. In this embodiment, preferably, the florasulam or the salt thereof is florasulam.

In the third aspect of the invention, it is yet more particularly preferred that the one or more agrochemically active ingredients (a) comprise (e.g. consist essentially of or are) one or more herbicides, wherein the one or more herbicides comprise:
  a combination of: (a1) pinoxaden, with (a2) florasulam or an agrochemically acceptable salt thereof, and optionally also with (a3) clodinafop-propargyl. In this embodiment, preferably, the florasulam or the salt thereof is florasulam.

In the third aspect of the invention, it is most preferred that the one or more agrochemically active ingredients (a) comprise (e.g. consist essentially of or are) one or more herbicides, wherein the one or more herbicides comprise:
  a combination of (a1) pinoxaden with (a2) florasulam, and optionally also with (a3) clodinafop-propargyl.

In the present invention, an alkylene carbonate means a cyclic alkanediyl diester of carbonic acid. In the present invention, a $(C_2$-$C_6$-alkylene) carbonate means a cyclic $C_2$-$C_6$-alkanediyl diester of carbonic acid. For example, 1,2-propylene carbonate is the cyclic propane-1,2-diyl diester of carbonic acid (also called propane-1,2-diol cyclic carbonate) and has the following structure:

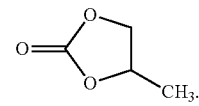

Preferably, in the third aspect of the invention, the liquid herbicidal composition, in particular in the form of an emulsifiable concentrate (EC), contains substantially no water (in particular less than 1% w/w of water, more particularly less than 0.5% w/w, e.g. equal to or less than 0.2% w/w, by weight of the liquid agrochemical e.g. herbicidal composition).

In a preferable embodiment of the invention, the features of the third and first, or third and second, or third and first and second, aspects of the invention are combined in a or the liquid agrochemical (e.g. herbicidal) composition.

A fourth aspect of the present invention provides a method for controlling and/or inhibiting the growth of weeds (in particular monocotyledonous weeds, more particularly grassy monocotyledonous weeds), the method comprising the following steps (a) and (b):

(a) mixing, in a container (e.g. in a tank such as a spray tank):
  (i) a liquid agrochemical composition according to the first and/or second and/or third aspect(s) of the invention, which is a first herbicidal composition, and in which the one or more agrochemically active ingredients comprise one or more herbicides,
  (ii) an agriculturally-acceptable aqueous solvent which is a carrier suitable for spraying the first herbicidal composition onto a field (preferably water), and (iii) optionally, one, two or more further herbicidal compositions each independently comprising one or more further herbicides,
to form a diluted aqueous liquid herbicidal composition; and
(b) applying (preferably spraying) the diluted aqueous liquid herbicidal composition to the weeds or to the locus thereof (in particular at a time after emergence of the weeds).

In the fourth aspect of the invention, the first, liquid, herbicidal composition is preferably in the form of an emulsifiable concentrate (EC).

In the fourth aspect of the invention, preferably, the first, liquid, herbicidal composition, e.g. in the form of an emulsifiable concentrate (EC), contains substantially no water (in particular less than 1% w/w of water, more particularly less than 0.5% w/w, e.g. equal to or less than 0.2% w/w, by weight of the first, liquid, herbicidal composition).

In one particular embodiment of the fourth aspect of the invention, in the method, the optional one, two or more further herbicidal compositions, which each independently comprise(s) one or more further herbicides, are present (i.e. are mixed in the container).

In the fourth aspect of the invention, preferably, the optional one or more further herbicides, if present (i.e. if mixed in the container), are suitable for controlling and/or inhibiting the growth of monocotyledonous and/or dicotyledonous weeds.

In all aspects (especially the fourth aspect) of the invention mentioned hereinabove or hereinbelow, when the one or more agrochemically active ingredients comprise pinoxaden, then, preferably, the liquid agrochemical (preferably herbicidal) composition (e.g. the diluted aqueous liquid herbicidal composition e.g. in the fourth aspect of the invention) is applied, at a time after emergence of the weeds, at an application rate of from 15 to 90 g/ha or preferably from 30 to 60 g/ha (more preferably 45 to 60 g/ha, most preferably 60 g/ha) of pinoxaden.

A fifth aspect of the invention provides the use of a $C_1$-$C_6$ alkyl methacrylate polymer as a thickener in a liquid agrochemical (preferably herbicidal) composition, in particular to increase the viscosity of the composition.

It is particularly preferable, in the fifth aspect of the invention, that the liquid agrochemical (preferably herbicidal) composition is in the form of an emulsifiable concentrate (EC), an oil dispersion (OD), a dispersible concentrate (DC), or a microemulsifiable concentrate. These are usually substantially-non-aqueous compositions.

Particularly preferably, the liquid agrochemical (e.g. herbicidal) composition is in the form of an emulsifiable concentrate (EC).

It is particularly preferable, in the fifth aspect of the invention, that the liquid agrochemical (preferably herbicidal) composition, in particular in the form of an emulsifiable concentrate (EC), contains substantially no water (in particular less than 1% w/w of water, more particularly less than 0.5% w/w, e.g. equal to or less than 0.2% w/w, by weight of the liquid agrochemical (preferably herbicidal) composition).

Preferably, in the fifth aspect of the invention, the liquid agrochemical composition is a liquid herbicidal composition containing pinoxaden (e.g. in the form of an emulsifiable concentrate (EC)), and the composition contains substantially no water (in particular less than 1% w/w of water, more particularly less than 0.5% w/w, e.g. equal to or less than 0.2% w/w of water).

Preferably, in the fifth aspect of the invention, the $C_1$-$C_6$ alkyl methacrylate polymer comprises (e.g. consists essentially of or is) a $C_3$-$C_6$ alkyl (or $C_3$-$C_5$ alkyl or $C_4$ alkyl) methacrylate polymer, more preferably an isobutyl methacrylate polymer.

Preferably, in the fifth aspect of the invention, the liquid agrochemical (e.g. herbicidal) composition contains heavy aromatic solvents, and the $C_1$-$C_6$ alkyl methacrylate polymer thickener is dissolved in the heavy aromatic solvents.

Preferred features of the first, second, third and/or fourth aspects of the invention are as follows. These preferred features also generally apply to the fifth and/or all other aspects of the present invention as described herein, with all necessary changes having been made.

Thickener

In the first aspect of the invention, and preferably in the second, third and/or fourth aspects of the invention, the composition contains a $C_1$-$C_6$ alkyl methacrylate polymer (preferably an isobutyl methacrylate polymer). This is present as a thickener, to increase the viscosity of the composition, for example as described above.

Preferably, in a or the liquid agrochemical (e.g. herbicidal and/or emulsifiable concentrate (EC)) composition containing heavy aromatic solvents, the thickener (preferably the $C_1$-$C_6$ alkyl methacrylate polymer) is dissolved in the heavy aromatic solvents (which usually contain inter alia $C_1$-$C_4$alkyl-naphthalenes). The thickener preferably being dissolved in the heavy aromatic solvents was mentioned hereinabove.

The thickener increases the viscosity of the liquid agrochemical (e.g. herbicidal and/or EC) composition. The increased viscosity reduces the potential for entry to the human lungs and any potential damage caused in the human lungs, after accidental oral ingestion of the liquid agrochemical (e.g. EC) composition, for example as described hereinabove.

Preferably, the $C_1$-$C_6$ alkyl methacrylate polymer is a $C_3$-$C_6$ alkyl methacrylate polymer, more preferably a $C_3$-$C_5$ alkyl methacrylate polymer, in particular a $C_4$ alkyl methacrylate polymer.

Still more preferably, the $C_1$-$C_6$ alkyl methacrylate polymer is an isobutyl methacrylate polymer.

Preferably, the $C_1$-$C_6$ alkyl (e.g. $C_3$-$C_6$ alkyl or $C_3$-$C_5$ alkyl, preferably isobutyl) methacrylate polymer:
has a molecular weight of from 40,000 to 400,000, more preferably from 60,000 to 300,000, in particular from 70,000 to 200,000 (e.g. about 80,000 or about 180,000); and/or
has a viscosity number of from 30 to 70, preferably from 35 to 60, in particular ca. 40 or ca. 55 or ca. 57, cm$^3$/g (measured using DIN 51 562); and/or
has a dynamic viscosity (measured when present at 40% in methyl ethyl ketone) of from 75 to 500, preferably from 100 to 400, more preferably from 120 to 300, in particular about 150 or about 200 or about 280, mPa·s; and/or
has a glass transition temperature (Tg) (measured using DIN 53 765) of from 40 to 80° C., more preferably from 45 to 70° C., in particular about 48° C. or about 65-66° C.

Most preferably, the $C_1$-$C_6$ alkyl methacrylate polymer is an isobutyl methacrylate polymer which is DEGALAN™ P 26 (e.g. available from Evonik Röhm GmbH, Germany). This is a bead polymer prepared by polymerization of isobutyl methacrylate. The properties of DEGALAN™ P 26 are: molecular weight 180,000; viscosity number 55 cm$^3$/g (measured using DIN 51 562); dynamic viscosity 150 mPa·s (measured at 40% in methyl ethyl ketone); and glass transition temperature (Tg) of 66° C. (measured using DIN 53 765).

In an alternative particularly preferable embodiment, the $C_1$-$C_6$ alkyl methacrylate polymer is an isobutyl methacrylate polymer which is DEGALAN™ P 28 (e.g. available from Evonik Röhm GmbH, Germany). This is a milled polymer prepared by polymerization of isobutyl methacrylate. The properties of DEGALAN™ P 28 are: molecular weight 80,000; viscosity number 40 cm³/g (measured using DIN 51 562); dynamic viscosity 200 mPa·s (measured at 40% in methyl ethyl ketone); and glass transition temperature (Tg) of 65° C. (measured using DIN 53 765).

In an alternative particularly preferable embodiment, the $C_1$-$C_6$ alkyl methacrylate polymer is an isobutyl methacrylate polymer which is DEGALAN™ P 675 (e.g. available from Evonik Röhm GmbH, Germany). This is a polymer in the form of pearls prepared by polymerization of isobutyl methacrylate. The properties of DEGALAN™ P 675 are: molecular weight 180,000; viscosity number 57 cm³/g (measured using DIN 51 562); dynamic viscosity 280 mPa·s (measured at 40% in methyl ethyl ketone); and glass transition temperature (Tg) of 48° C. (measured using DIN 53 765).

Preferably, the $C_1$-$C_6$ alkyl methacrylate polymer (e.g. $C_3$-$C_6$ alkyl methacrylate polymer, e.g. isobutyl methacrylate polymer) is present in from 0.5% to 7% or from 1% to 7% or from 1% to 6% or from 1% to 5%, more preferably from 1.5% to 7% or from 1.5% to 6% or from 1.5% to 5% or from 1.5% to 4%, still more preferably from 2% to 7% or from 2% to 6% or from 2% to 5% or from 2% to 4% or from 2.2% to 4%, most preferably from 2.2% to 5% or from 2.2% to 4.5% or from 2.2% to 3.7%, in particular about 2.5%, about 3.5%, about 3.75%, about 4.0% or about 4.25%, by weight of the liquid (or first) agrochemical composition.

In the first, second, third, fourth, fifth and/or other aspects of the invention, it is strongly preferred that the kinematic viscosity of the liquid (or first) agrochemical (e.g. herbicidal) composition, measured at 40° C., is 20.5 mm²/second or more; this is typically as measured by a rheometer or viscosimeter, preferably a Rheoplus Physica™ MCR 301 rheometer (e.g. available from Anton Paar) or a functionally-equivalent rheometer or viscosimeter. For such viscosity measurements, measurements of viscosity are taken at different rotational speeds of the composition at a specified tested temperature (preferably 40° C.), which typically show the dependency of the viscosity on the rotational speed (or shear rate), e.g. in the viscosimeter or rheometer, at the tested temperature. The kinematic viscosity is determined (e.g. by the viscosimeter or rheometer) by dividing the absolute viscosity by the density of the fluid.

A typical method for measuring kinematic viscosity, e.g. of a or the liquid (or first) agrochemical (e.g. herbicidal) composition, is as follows. This method is and/or has been used by the patent applicant in the laboratory. Preferably, a Rheoplus Physica™ MCR 301 rheometer or viscosimeter (e.g. available from Anton Paar), or a functionally-equivalent rheometer or viscosimeter, is used. Approximately 80 mL (or, alternatively, approximately 19 mL) of the liquid (or first) agrochemical (e.g. herbicidal) composition is transferred to a or the cylinder of the viscosimeter (or rheometer). The spindle of the viscosimeter (or rheometer) is then submerged and the sample of the composition is heated up to 40° C. and kept at this temperature for 30 minutes. Then, the spindle starts rotation with gradually increasing speed (rotational speed or shear rate), starting from 0 s$^{-1}$ and gradually increasing to 300 s$^{-1}$ (preferably within 120 seconds); when the maximum rotation is reached the spindle slows down from 300 s$^{-1}$ to 0 s$^{-1}$ while measuring and documenting various measurement points of viscosity at different rotational speeds. After cooling down to 20° C. one can remove the sample of the composition. In such viscosity measurements, the measurement points show the dependency of the viscosity on the rotational speed (or shear rate) of the composition, at the tested temperature. The viscosimeter (or rheometer) determines the kinematic viscosity by dividing the absolute viscosity by the density of the fluid.

Usually in this specification, kinematic viscosities at 40° C. are presented which have been calculated by dividing the absolute viscosity (measured at 40° C.) by the density of the fluid (measured at 23° C. and not at 40° C., for convenience).

A suitable method for measuring density is OECD Guideline for the Testing of Chemicals No. 109 (1995) ["OECD 109"], according to which: The density is determined by means of an oscillating density meter. The measuring equipment is calibrated using deionized water and air. The test sample is injected by a syringe into the density meter where the sample is equilibrated to the appropriate temperature. Then the reading of the density meter is recorded.

Solvent System 1—(c1) Alcohol Solvent and (c2) Heavy Aromatic Hydrocarbon Solvent Generally in the first aspect of the invention, and in a preferable embodiment of the second, third and/or fourth aspects of the invention, the liquid agrochemical (e.g. herbicidal) composition comprises:

(c) a solvent system comprising:

(c1) an alcohol solvent comprising (e.g. consisting essentially of or being) hexylene glycol (2-methyl-2,4-pentanediol), benzyl alcohol, diacetone alcohol (2-methyl-4-oxo-pentane-2-ol, or 4-hydroxy-4-methyl-2-pentanone), isobutanol, n-pentanol, n-hexanol, n-heptanol, n-octanol, 2-ethyl-hexanol, cyclohexanol, dipropylene glycol, diethylene glycol monomethyl ether, dipropylene glycol monomethyl ether, ethylene glycol, or a mixture of two or more of these alcohols; and (c2) a heavy aromatic hydrocarbon solvent.

Preferably, the alcohol solvent (c1) comprises (e.g. consists essentially of or is) hexylene glycol (2-methyl-2,4-pentanediol), benzyl alcohol, diacetone alcohol (2-methyl-4-oxo-pentane-2-ol, or 4-hydroxy-4-methyl-2-pentanone), isobutanol, n-hexanol, n-octanol, 2-ethyl-hexanol, cyclohexanol, dipropylene glycol, diethylene glycol monomethyl ether, dipropylene glycol monomethyl ether, ethylene glycol, or a mixture of two or more of these alcohols.

More preferably, the alcohol solvent (c1) comprises (e.g. consists essentially of or is) hexylene glycol (2-methyl-2,4-pentanediol), benzyl alcohol, diacetone alcohol (2-methyl-4-oxo-pentane-2-ol, or 4-hydroxy-4-methyl-2-pentanone), n-hexanol, n-octanol, 2-ethyl-hexanol, cyclohexanol, dipropylene glycol, diethylene glycol monomethyl ether, dipropylene glycol monomethyl ether, or a mixture of two or more of these alcohols.

Even more preferably, the alcohol solvent (c1) comprises (e.g. consists essentially of or is) hexylene glycol (2-methyl-2,4-pentanediol), benzyl alcohol, diacetone alcohol (2-methyl-4-oxo-pentane-2-ol, or 4-hydroxy-4-methyl-2-pentanone), n-hexanol, diethylene glycol monomethyl ether, or a mixture of two or more of these alcohols.

Yet more preferably, the alcohol solvent (c1) comprises (e.g. consists essentially of or is) hexylene glycol (2-methyl-2,4-pentanediol), benzyl alcohol, diacetone alcohol (2-methyl-4-oxo-pentane-2-ol, or 4-hydroxy-4-methyl-2-pentanone), or a mixture of two or more of these alcohols.

Most preferably, the alcohol solvent (c1) comprises (e.g. consists essentially of or is) hexylene glycol (2-methyl-2,4-pentanediol).

Preferably, in all aspect of the invention, a or the alcohol solvent (preferably alcohol solvent (c1) as defined above) is typically present in from 5% to 50% or from 8% to 45% by weight of the liquid (or first) agrochemical (e.g. herbicidal) composition; but more preferably a or the alcohol solvent (preferably alcohol solvent (c1) as defined above) is present in from 10% to 40% or from 15% to 40% or from 16% to 40%, still more preferably from 15% to 30% or from 16% to 30%, most preferably from 16% to 25%, by weight of the liquid (or first) agrochemical (e.g. herbicidal) composition (e.g. EC).

In the first aspect of the invention, and in a preferable embodiment of the second, third and/or fourth aspects of the invention, the liquid (or first) agrochemical (e.g. herbicidal) composition (e.g. EC) comprises a heavy aromatic hydrocarbon solvent (named component "(c2)"). The heavy aromatic hydrocarbon solvent is typically a mixture of heavy aromatic hydrocarbons. More preferably, the heavy aromatic hydrocarbon solvent comprises a mixture of naphthalenes substituted by alkyl(s), wherein the alkyl(s) contain 1, 2, 3 or 4 or more (e.g. 1, 2, 3 or 4) carbon atoms in total (i.e. per substituted naphthalene molecule). Still more preferably, the naphthalenes substituted by alkyl(s) are present in a total of from 50% to 100%, preferably from 65% to 99%, more preferably from 75% to 97%, by weight of the heavy aromatic hydrocarbon solvent. Preferably, the heavy aromatic hydrocarbon solvent has a low content of naphthalene (i.e. unsubstituted naphthalene); and more preferably contains from 0% to 2% or from 0% to 1% of naphthalene, more preferably from 0.01% to 1% of naphthalene, such as from 0.05% to 0.7% of naphthalene, by weight of the heavy aromatic hydrocarbon solvent; this is typically called a "naphthalene-depleted" heavy aromatic hydrocarbon solvent.

In one particularly preferred embodiment, the heavy aromatic hydrocarbon solvent comprises (e.g. consists essentially of, or is) Solvesso™ 200 ND, e.g. available from Exxon, Europe. Solvesso™ 200 ND typically has a low percentage (e.g. ca. 0.5%) of (unsubstituted) naphthalene (ND=naphthalene depleted), and comprises also varying percentages of other (e.g. higher) aromatic hydrocarbons, and in particular typically comprises naphthalenes substituted by alkyl(s) wherein the alkyl(s) contain 1, 2, 3 or 4 or more (e.g. 1, 2 or 3) carbon atoms in total (i.e. per substituted naphthalene molecule). By way of example only, certain batches of Solvesso 200 ND™ have been measured by Syngenta (in 2010 or beforehand) as comprising, very approximately, the following ingredients: ca. 0.5% of naphthalene, ca. 14% to ca. 22% of 1-methyl-naphthalene, ca. 14% to ca. 32% of 2-methyl-naphthalene, ca. 21% to ca. 25% of $C_2$-naphthalene (i.e. molecule(s) containing naphthalene+two additional carbon atoms, e.g. ethyl-naphthalene and/or dimethyl-naphthalene), ca. 9% to ca. 17% of $C_3$-naphthalene (i.e. molecule(s) containing naphthalene+three additional carbon atoms), 0% to ca. 11% of ($C_4$ and/or higher)-naphthalene(s) (i.e. molecule(s) containing naphthalene+four and/or more additional carbon atoms), ca. 0.05% to ca. 0.5% of biphenyl, 0% to ca. 5% of $C_4$-benzene (i.e. molecule(s) containing benzene+four additional carbon atoms), and 0% to ca. 3% of $C_5$-benzene (i.e. molecule(s) containing benzene+five additional carbon atoms); and typically these mentioned ingredients form ca. 75% to ca. 97% by weight of the Solvesso™ 200 ND heavy aromatic hydrocarbon solvent.

In an alternative particularly preferred embodiment, the heavy aromatic hydrocarbon solvent comprises (e.g. consists essentially of, or is) Aromatic™ 200 ND, e.g. available from Exxon, USA. Aromatic™ 200 ND typically has a low percentage (e.g. ca. 0.1% to 0.3%) of (unsubstituted) naphthalene (ND=naphthalene depleted), and comprises also varying percentages of other (e.g. higher) aromatic hydrocarbons, and in particular typically comprises naphthalenes substituted by alkyl(s) wherein the alkyl(s) contain 1, 2 or 3 carbon atoms in total (i.e. per substituted naphthalene molecule). By way of example only, certain batches of Aromatic 200 ND™ have been measured by Syngenta (in 2010 or beforehand) as comprising, very approximately, the following ingredients: ca. 0.1% to ca. 0.2% of naphthalene, ca. 16% to ca. 20% of 1-methyl-naphthalene, ca. 30% to ca. 34% of 2-methyl-naphthalene, ca. 28% to ca. 30% of $C_2$-naphthalene (i.e. molecule(s) containing naphthalene+two additional carbon atoms, e.g. ethyl-naphthalene and/or dimethyl-naphthalene), 0% to ca. 10% of $C_3$-naphthalene (i.e. molecule(s) containing naphthalene+three additional carbon atoms), ca. 0.4% to ca. 0.5% of biphenyl; and typically these mentioned ingredients form ca. 75% to ca. 97% by weight of the Aromatic™ 200 ND heavy aromatic hydrocarbon solvent.

The heavy aromatic hydrocarbon solvent is typically present in from 8% to 50% by weight of the liquid (or first) agrochemical (e.g. herbicidal) composition, but preferably it is present in from 10% to 45% or from 15% to 40%, more preferably from 15% to 35%, in particular from 20% to 30%, by weight of the liquid (or first) agrochemical (e.g. herbicidal) composition (e.g. EC).

Preferably, e.g. as described above, the liquid (or first) agrochemical (e.g. herbicidal) composition (e.g. EC) comprises a heavy aromatic hydrocarbon solvent (e.g. as described herein) and an alcohol solvent [e.g. as described herein]. The weight ratio of the heavy aromatic hydrocarbon solvent to the alcohol solvent is preferably from 4:1 to 0.3:1, more typically from 3:1 to 0.5:1 or from 2.5:1 to 0.7:1. However, in particular in order possibly to maximise the stability and/or properties of the composition such as an EC, more preferably, the weight ratio of the heavy aromatic hydrocarbon solvent to the alcohol solvent is from 1.7:1 to 0.3:1 or from 1.7:1 to 0.5:1, more preferably from 1.5:1 to 0.5:1 or from 1.5:1 to 0.7:1, still more preferably from 1.35:1 to 0.8:1, e.g. from 1.25:1 to 1.0:1.

Solvent System 2—Solvent (c3) Alkylene Carbonate and (c1a) Alcohol Solvent

Generally in the third aspect of the present invention, and optionally in other aspects of the invention, the liquid agrochemical (preferably herbicidal) composition, preferably in the form of an emulsifiable concentrate (EC), comprises:

(c) a solvent system comprising:
(c3) a ($C_2$-$C_6$-alkylene) carbonate; and
(c1a) an alcohol solvent comprising (e.g. consisting essentially of or being) hexylene glycol (2-methyl-2,4-pentanediol), benzyl alcohol, diacetone alcohol (2-methyl-4-oxo-pentane-2-ol, or 4-hydroxy-4-methyl-2-pentanone), isobutanol, n-pentanol, n-hexanol, n-heptanol, n-octanol, 2-ethyl-hexanol, cyclohexanol, dipropylene glycol, diethylene glycol monomethyl ether, dipropylene glycol monomethyl ether, or a mixture of two or more of these alcohols.

In the present invention, an alkylene carbonate means a cyclic alkanediyl diester of carbonic acid. In the present invention, a ($C_2$-$C_6$-alkylene) carbonate means a cyclic $C_2$-$C_6$-alkanediyl diester of carbonic acid. For example, 1,2-propylene carbonate is the cyclic propane-1,2-diyl diester of carbonic acid (also called propane-1,2-diol cyclic carbonate) and has the following structure:

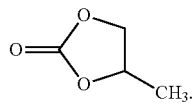

Preferably, in the third and/or other alkylene carbonate containing aspects of the invention, the ($C_2$-$C_6$-alkylene) carbonate (c3) has a five- or six-membered, more preferably five-membered, ring.

Preferably, in the third and/or other alkylene carbonate containing aspects of the invention, the ($C_2$-$C_6$-alkylene) carbonate (c3) comprises (e.g. consists essentially of or is) a ($C_2$-$C_5$-alkylene) or ($C_2$-$C_4$-alkylene) carbonate, more preferably a ($C_3$-$C_5$-alkylene) or ($C_3$-$C_4$-alkylene) carbonate. Preferably, the ($C_2$-$C_6$-alkylene) carbonate (such as a ($C_2$-$C_5$-alkylene) or ($C_2$-$C_4$-alkylene) carbonate) comprises (e.g. consists essentially of or is) ethylene carbonate, 1,2-propylene carbonate, 1,3-propylene carbonate, 1,2-butylene carbonate, 1,3-butylene carbonate, 2,3-butylene carbonate, 1,2-pentylene carbonate, 1,3-pentylene carbonate, 2,3-pentylene carbonate, 2,4-pentylene carbonate, 1,2-hexylene carbonate, 2-methyl-2,4-pentylene carbonate, or a mixture of two or more of these carbonates. More preferably, the ($C_2$-$C_6$-alkylene) carbonate (such as a ($C_2$-$C_5$-alkylene) or ($C_2$-$C_4$-alkylene) carbonate) comprises (e.g. consists essentially of or is) 1,2-propylene carbonate, 1,2-butylene carbonate, or a mixture thereof; or most preferably 1,2-propylene carbonate.

Preferably, in the third and/or other alkylene carbonate containing aspects of the invention, the ($C_2$-$C_6$-alkylene) or ($C_2$-$C_5$-alkylene) or ($C_2$-$C_4$-alkylene) or ($C_3$-$C_5$-alkylene) or ($C_3$-$C_4$-alkylene) carbonate (c3) is typically present in from 3% to 80% or from 3% to 50% or from 3% to 40% or from 5% to 80% or from 5% to 50% or from 5% to 40% by weight of the liquid (or first) agrochemical (e.g. herbicidal) composition. More preferably, the alkylene (e.g. ($C_2$-$C_6$-alkylene)) carbonate solvent (e.g. as defined herein) is present in from 7% to 40% or from 8% to 30%, still more preferably from 9% to 25%, most preferably from 10% to 25% or from 10% to 20%, by weight of the liquid (or first) agrochemical (e.g. herbicidal) composition (e.g. EC).

Preferably, in the third and/or other alkylene carbonate containing aspects of the invention, in addition to the ($C_2$-$C_6$-alkylene) carbonate (c3) and the alcohol solvent (c1a), the solvent system also comprises:

(c2) a heavy aromatic hydrocarbon solvent.

More preferably, in the third and/or other alkylene carbonate containing aspects of the invention, in addition to the ($C_2$-$C_6$-alkylene) carbonate (c3), the solvent system also comprises the alcohol solvent (c1a) and a heavy aromatic hydrocarbon solvent (c2).

In the third and/or other alkylene carbonate containing aspects of the invention, a or the heavy aromatic hydrocarbon solvent (c2) can be as defined elsewhere herein, e.g. as defined for preferred embodiment(s) of component (c2) of the first aspect of the invention.

Preferably, in the third and/or other alkylene carbonate containing aspects of the invention, the solvent system comprises an alcohol solvent (c1a) which is the alcohol solvent (c1) as defined elsewhere herein (e.g. as defined herein as component (c1) of the first aspect of the invention), except that ethylene glycol and tetrahydrofurfuryl alcohol ("THFA") are not mentioned in the list of alcohol solvents within the alcohol solvent (c1a).

Preferably, in the third and/or other alkylene carbonate containing aspects of the invention, the alcohol solvent (c1a) comprises (e.g. consists essentially of or is) hexylene glycol (2-methyl-2,4-pentanediol), benzyl alcohol, diacetone alcohol (2-methyl-4-oxo-pentane-2-ol, or 4-hydroxy-4-methyl-2-pentanone), n-pentanol, n-hexanol, n-heptanol, n-octanol, 2-ethyl-hexanol, cyclohexanol, dipropylene glycol, diethylene glycol monomethyl ether, dipropylene glycol monomethyl ether, or a mixture of two or more of these alcohols.

More preferably, in the third and/or other alkylene carbonate containing aspects of the invention, the alcohol solvent (c1a) or (c1) comprises (e.g. consists essentially of or is) hexylene glycol (2-methyl-2,4-pentanediol), benzyl alcohol, diacetone alcohol (2-methyl-4-oxo-pentane-2-ol, or 4-hydroxy-4-methyl-2-pentanone), n-hexanol, n-octanol, 2-ethyl-hexanol, cyclohexanol, dipropylene glycol, diethylene glycol monomethyl ether, dipropylene glycol monomethyl ether, or a mixture of two or more of these alcohols. Even more preferably, in the third and/or other alkylene carbonate containing aspects of the invention, the alcohol solvent (c1a) or (c1) comprises (e.g. consists essentially of or is) hexylene glycol (2-methyl-2,4-pentanediol), benzyl alcohol, diacetone alcohol (2-methyl-4-oxo-pentane-2-ol, or 4-hydroxy-4-methyl-2-pentanone), n-hexanol, n-octanol, 2-ethyl-hexanol, cyclohexanol, diethylene glycol monomethyl ether, or a mixture of two or more of these alcohols. Still more preferably, in this embodiment, the alcohol solvent (c1a) or (c1) comprises (e.g. consists essentially of or is) hexylene glycol (2-methyl-2,4-pentanediol), benzyl alcohol, diacetone alcohol (2-methyl-4-oxo-pentane-2-ol, or 4-hydroxy-4-methyl-2-pentanone), or a mixture of two or more of these alcohols. Most preferably, in this embodiment, the alcohol solvent (c1a) or (c1) comprises (e.g. consists essentially of or is) benzyl alcohol.

More preferably, in the third and/or other alkylene carbonate containing aspects of the invention, the solvent system (c) comprises:

(c3) a ($C_2$-$C_4$-alkylene) or ($C_3$-$C_4$-alkylene) carbonate, in particular comprising (e.g. consisting essentially of or being) 1,2-propylene carbonate, 1,2-butylene carbonate, or a mixture thereof; and (c1a) an alcohol solvent comprising (e.g. consisting essentially of or being) benzyl alcohol; and preferably also (c2) a heavy aromatic hydrocarbon solvent.

Preferably, in the third and/or other alkylene carbonate containing aspects of the invention where the alcohol solvent (c1a) or (c1) is present, the alcohol solvent (c1a) or (c1) is typically present in from 3% to 50% or from 3% to 40% or from 5% to 50% or from 5% to 40% by weight of the liquid (or first) agrochemical (e.g. herbicidal) composition. More preferably, the alcohol solvent (c1a) or (c1) (e.g. as defined herein, most preferably benzyl alcohol) is present in from 7% to 40% or from 8% to 30%, still more preferably from 9% to 25%, most preferably from 10% to 25% or from 10% to 20%, by weight of the liquid (or first) agrochemical (e.g. herbicidal) composition (e.g. EC).

Preferably, in the third and/or other alkylene carbonate containing aspects of the invention, when the alcohol solvent (c1a) or (c1) is present (which is preferable), then the weight ratio (or volume ratio) of the ($C_2$-$C_6$-alkylene) or ($C_2$-$C_5$-alkylene) or ($C_2$-$C_4$-alkylene) or ($C_3$-$C_5$-alkylene) or ($C_3$-$C_4$-alkylene) carbonate (c3) to the alcohol solvent (c1a) or (c1) (such as benzyl alcohol) is from 10:1 to 1:10, more preferably from 5:1 to 1:5, still more preferably from 3:1 to 1:3, yet more preferably from 2:1 to 1:2, further more preferably from 3:2 to 2:3, most preferably about 1:1.

Preferably, in the third and/or other alkylene carbonate containing aspects of the invention, when the heavy aromatic hydrocarbon solvent (c2) is present (which is preferable), then the weight ratio (or volume ratio) of the ($C_2$-$C_6$-alkylene) or ($C_2$-$C_5$-alkylene) or ($C_2$-$C_4$-alkylene) or ($C_3$-$C_5$-alkylene) or ($C_3$-$C_4$-alkylene) carbonate (c3) to the heavy aromatic hydrocarbon solvent (c2) is from 10:1 to 1:12, more preferably from 4:1 to 1:6, still more preferably from 3:1 to 2:7, yet more preferably from 2:1 to 1:3, further more preferably from 3:2 to 1:2, most preferably from 1:1 to 2:3.

Preferably, in the third and/or other alkylene carbonate containing aspects of the invention, when the heavy aromatic hydrocarbon solvent (c2) is present, it is preferably present in the composition in percentage ranges by weight of the liquid (or first) agrochemical (e.g. herbicidal) composition as defined elsewhere herein for the heavy aromatic hydrocarbon solvent (c2), e.g. as defined hereinabove for the preferred embodiments of the solvent system of e.g. the first aspect of the invention (e.g. see section on Solvent system 1 hereinabove).

In the third and/or other alkylene carbonate containing aspects of the invention, it is particularly preferred that the one or more agrochemically active ingredients (a) comprise (e.g. consist essentially of or are) one or more herbicides, wherein the one or more herbicides comprise:
(a1) pinoxaden; or (a2) florasulam or an agrochemically acceptable salt thereof; or (a3) clodinafop-propargyl; or a combination of (a2) florasulam or an agrochemically acceptable salt thereof with (a1) pinoxaden and/or (a3) clodinafop-propargyl.

In the third and/or other alkylene carbonate containing aspects of the invention, it is even more particularly preferred that the one or more agrochemically active ingredients (a) comprise (e.g. consist essentially of or are) one or more herbicides, wherein the one or more herbicides comprise:
(a1) pinoxaden; or (a2) florasulam or an agrochemically acceptable salt thereof; or a combination of: (a1) pinoxaden, with (a2) florasulam or an agrochemically acceptable salt thereof, and optionally also with (a3) clodinafop-propargyl.

In the third and/or other alkylene carbonate containing aspects of the invention, it is preferred that:
if pinoxaden is present, then the composition comprises from 0.5% to 30% (preferably from 1% to 20%, most preferably from 2% to 10%) of pinoxaden by weight of the liquid (or first) agrochemical (e.g. herbicidal) composition (e.g. EC); and
if florasulam or an agrochemically acceptable salt thereof is present, then it is present in from 0.05% to 10% (preferably from 0.1% to 5% or from 0.2% to 3%), of (preferably by weight of) the liquid (or first) agrochemical (e.g. herbicidal) composition (e.g. EC); and
if clodinafop-propargyl is present, then it is present in from 0.5% to 10% (preferably from 1% to 5%), of (preferably by weight of) the liquid (or first) agrochemical (e.g. herbicidal) composition (e.g. EC).

It is believed that this alkylene carbonate containing solvent system is suitable or particularly suitable for liquid agrochemical (e.g. herbicidal) compositions (e.g. ECs) comprising pinoxaden, florasulam or an agrochemically acceptable salt thereof, or clodinafop-propargyl, or (more preferably) a combination of pinoxaden, and florasulam or an agrochemically acceptable salt thereof, and optionally clodinafop-propargyl. Details are discussed hereinabove in the section where the third aspect of the invention is first discussed. It was time-consuming and difficult to discover that the present solvent system was a suitable solvent system (which did not require tetrahydrofurfuryl alcohol ("THFA")) for pinoxaden and florasulam or an agrochemically acceptable salt thereof, especially considering special and/or difficult considerations regarding solubilizing florasulam.

Preferred Built-in Phosphate and/or Phosphonate Adjuvant

Preferably, in all aspects of the invention, the composition comprises a built-in phosphate and/or phosphonate adjuvant, wherein the built-in phosphate and/or phosphonate adjuvant comprises a tris-[$C_4$-$C_{12}$alkyl or 2-($C_2$-$C_6$alkoxy)$C_2$-$C_4$alkyl-]ester of phosphoric acid and/or a bis-($C_3$-$C_{12}$alkyl) ester of a $C_3$-$C_{12}$alkyl-phosphonic acid.

Alkyl and alkoxyalkyl groups, e.g. within the phosphate and/or phosphonate adjuvant (and/or within any ester groups contained within any non-pinoxaden herbicides present), can be straight-chain (linear) or branched. Where two or three or more alkyl and/or alkoxyalkyl groups are present within the phosphate and/or phosphonate adjuvant, these can be the same or different.

For the built-in phosphate and/or phosphonate adjuvant, preferably, the tris-ester of phosphoric acid is a tris-[$C_6$-$C_{10}$alkyl or 2-($C_2$-$C_6$alkoxy)ethyl-]ester of phosphoric acid, in particular a tris-[$C_8$alkyl or 2-($C_4$alkoxy)ethyl-]ester of phosphoric acid. More preferably, the tris-ester of phosphoric acid is tris-(2-ethylhexyl)phosphate, tris-n-octyl phosphate and/or tris-[2-(n-butoxy)ethyl]phosphate; most preferably tris-(2-ethylhexyl)phosphate (whose abbreviation is TEHP).

For the built-in phosphate and/or phosphonate adjuvant, preferably, the bis-ester of the $C_3$-$C_{12}$alkyl-phosphonic acid is a bis-($C_4$-$C_{10}$alkyl) ester of a $C_4$-$C_{10}$alkyl-phosphonic acid, in particular a bis-($C_4$-$C_8$alkyl) ester of a $C_4$-$C_8$alkyl-phosphonic acid. More preferably, the bis-ester of the $C_3$-$C_{12}$alkyl-phosphonic acid is: bis-(2-ethylhexyl) (2-ethylhexyl)phosphonate, bis-(2-ethylhexyl) (n-octyl)phosphonate and/or di-n-butyl(n-butyl)phosphonate; most preferably bis-(2-ethylhexyl) (n-octyl)phosphonate.

Preferably, the built-in phosphate and/or phosphonate adjuvant comprises (e.g. consists essentially of) tris-(2-ethylhexyl)phosphate, tris-n-octyl phosphate, tris-[2-(n-butoxy)ethyl]phosphate, bis-(2-ethylhexyl) (2-ethylhexyl)phosphonate, bis-(2-ethylhexyl) (n-octyl)phosphonate and/or di-n-butyl(n-butyl)phosphonate.

Preferably, the built-in phosphate and/or phosphonate adjuvant is a built-in phosphate adjuvant.

Most preferably, the built-in phosphate and/or phosphonate adjuvant comprises (e.g. consists essentially of) tris-(2-ethylhexyl)phosphate (whose abbreviation is TEHP).

Typically, the built-in phosphate and/or phosphonate adjuvant is present in from 5% to 70% by weight of the liquid (or first) agrochemical (e.g. herbicidal) composition; but preferably it is present in from 10% to 60%, more preferably from 15% to 50%, still more preferably from 20% to 50% or from 20% to 45%, most preferably from 20% to 40% or from 25% to 40%, by weight of the liquid (or first) agrochemical (e.g. herbicidal) composition (e.g. EC).

Active Ingredients

In all aspects of the invention mentioned hereinabove or hereinbelow, preferably, the liquid (or first) agrochemical (preferably herbicidal) composition (e.g. EC) comprises from 0.05% to 30%, preferably from 0.2% to 20%, most preferably from 0.5% to 12%, of the total of the one or more agrochemically active ingredients, by weight of the liquid (or first) agrochemical (e.g. herbicidal) composition (e.g. EC).

In all aspects of the invention, preferably, the liquid (or first) agrochemical composition is a herbicidal composition.

Preferably, the one or more agrochemically active ingredients comprise one or more herbicides.

Preferably, the one or more agrochemically active ingredients comprise one or more herbicides selected from the group consisting of: 2-aryl- or 2-heteroaryl-cyclic 3-keto-1-en-1-ols (2-aryl- or 2-heteroaryl-cyclic 1,3-diones) and ester or carbonate derivatives thereof (preferably pinoxaden), aryloxyphenoxy propionic acids and esters thereof, heteroaryloxyphenoxy propionic acids and esters thereof (preferably clodinafop-propargyl, fenoxaprop-P-ethyl or fluazifop-P-butyl, or alternatively e.g. diclofop-methyl), cyclohexanediones (e.g. tralkoxydim), sulfonyl ureas, sulfonylamino-carbonyl-triazolinones, triazolopyrimidines (e.g. triazolopyrimidine sulfonamides, such as pyroxsulam, florasulam, penoxsulam, metosulam, flumetsulam, diclosulam, or cloransulam-methyl), imidazolinones, pyrimidinyl (thio or oxy) benzoates, nitriles, thiocarbamates, dinitroanilines, benzoic acids, pyridine carboxylic acids, phenoxy acids (e.g. phenoxy carboxylic acids), and HPPD inhibitor herbicides.

More preferably, the one or more agrochemically active ingredients comprise one or more herbicides selected from pinoxaden, clodinafop-propargyl, fenoxaprop-P-ethyl, fluazifop-P-butyl, tralkoxydim, prosulfocarb, triasulfuron, prosulfuron, amidosulfuron, iodosulfuron (e.g. iodosulfuron-methyl-sodium), chlorsulfuron, flupyrsulfuron, mesosulfuron (e.g mesosulfuron-methyl), metsulfuron, sulfosulfuron, thifensulfuron, tribenuron (e.g. tribenuron-methyl), tritosulfuron, pyroxsulam, florasulam, penoxsulam, metosulam, flumetsulam, 2,4-D, 2,4-DP, dichlorprop-p, MCPA, mecoprop, mecoprop-p, MCPB, clopyralid, bromoxynil, bromoxynil octanoate, ioxynil, ioxynil octanoate, fluroxypyr or an ester (e.g. $C_1$-$C_{10}$ alkyl ester) thereof (e.g. fluroxypyr-meptyl, which is the 1-methylheptyl ester of fluroxypyr), trifluralin, diflufenican, picolinafen, pendimethalin, and triallate, and (where appropriate and/or possible) esters e.g. $C_1$-$C_{10}$ (e.g. $C_1$-$C_{10}$ alkyl) esters thereof and/or agrochemically acceptable salts thereof. Alternatively or additionally, the one or more agrochemically active ingredients comprise one or more herbicides selected from: the above list of herbicides [including (where appropriate and/or possible) esters, e.g. $C_1$-$C_{10}$ (e.g. $C_1$-$C_{10}$ alkyl) esters, thereof and/or agrochemically acceptable salts thereof], diclosulam or an agrochemically acceptable salt thereof, cloransulam-methyl, an agrochemically acceptable salt or ester (e.g. $C_1$-$C_{10}$ alkyl ester) of dicamba, bromoxynil heptanoate, pyrasulfotole or an agrochemically acceptable salt thereof, topramezone or an agrochemically acceptable salt thereof, bicyclopyrone or an agrochemically acceptable salt thereof, pyroxasulfone or an agrochemically acceptable salt thereof, and metribuzin or an agrochemically acceptable salt thereof.

Still more preferably, the one or more agrochemically active ingredients comprise one or more herbicides selected from: pinoxaden, clodinafop-propargyl, fenoxaprop-P-ethyl, prosulfocarb, pyroxsulam or an agrochemically acceptable salt thereof, florasulam or an agrochemically acceptable salt thereof, metosulam or an agrochemically acceptable salt thereof, bromoxynil octanoate, ioxynil octanoate, and an ester (e.g. a $C_1$-$C_{10}$ alkyl ester) of fluroxypyr (e.g. fluroxypyr-meptyl).

Still more preferably, the one or more agrochemically active ingredients comprise one or more herbicides selected from: pinoxaden, clodinafop-propargyl, fenoxaprop-P-ethyl, pyroxsulam or an agrochemically acceptable salt thereof, florasulam or an agrochemically acceptable salt thereof, and an ester (e.g. a $C_1$-$C_{10}$ alkyl ester) of fluroxypyr (e.g. fluroxypyr-meptyl).

Yet more preferably, the one or more agrochemically active ingredients comprise one or more herbicides selected from: pinoxaden, clodinafop-propargyl, and florasulam or an agrochemically acceptable salt thereof.

Most preferably, the one or more agrochemically active ingredients comprise pinoxaden. In this most preferred embodiment, the one or more agrochemically active ingredients optionally also comprise clodinafop-propargyl and/or florasulam or an agrochemically acceptable salt thereof.

Optionally, clodinafop-propargyl (a further herbicide, suitable for controlling grassy weeds), can also be incorporated into the liquid (or first) agrochemical (preferably herbicidal) compositions (e.g. EC's) according to, or used in, the present invention. Clodinafop-propargyl can for example be present in from 0.5% to 10%, in particular from 1% to 5%, of (preferably by weight of) the liquid (or first) agrochemical (preferably herbicidal) composition (e.g. EC).

Optionally, florasulam or an agrochemically acceptable salt thereof (a further herbicide, suitable for controlling broadleaved and/or dicotyledonous weeds), can also be incorporated into the liquid (or first) agrochemical (preferably herbicidal) compositions (e.g. EC's) according to, or used in, the present invention. Florasulam or an agrochemically acceptable salt thereof can for example be present in from 0.05% to 10%, in particular from 0.1% to 5% or from 0.2% to 3%, of (preferably by weight of) the liquid (or first) agrochemical (preferably herbicidal) composition (e.g. EC).

In all aspect of the present invention, it is strongly preferable that the liquid (or first) agrochemical (preferably herbicidal) composition according to, or used in, the present invention contains a safener. Preferably, the safener is selected from the group consisting of cloquintocet-mexyl, cloquintocet acid, mefenpyr-diethyl, cyprosulfamide, isoxadifen-ethyl and mixtures thereof; most preferably the safener is cloquintocet-mexyl. These safeners are known and are described, for example, in The Pesticide Manual, 15$^{th}$ Edition, British Crop Protection Council, 2009 or other readily available resources. Preferably, the safener (e.g. cloquintocet-mexyl) is present in from 0.1% to 10%, preferably from 0.5% to 5%, more preferably from 0.5% to 3%, e.g. from 0.7% to 2%, e.g. from 1.0% to 1.5%, by weight of the liquid (or first) agrochemical (preferably herbicidal) composition (e.g. EC). Typically, the weight ratio of the one or more herbicides to the safener, in particular the weight ratio of [the pinoxaden and/or the clodinafop-propargyl and/or the pyroxsulam] to the safener, in particular the weight ratio of the pinoxaden to the safener such as the weight ratio of the pinoxaden to the [cloquintocet-mexyl or cloquintocet acid], is from 30:1 to 1:2, preferably from 20:1 to 1:1, more preferably from 8:1 to 2:1, most preferably 4:1.

Preferred Aspects for Pinoxaden-Containing Compositions

In all aspects of the invention mentioned hereinabove or hereinbelow, independently, especially preferably, the liquid (or first) agrochemical (preferably herbicidal) composition (e.g. EC) comprises from 0.5% to 30% pinoxaden, preferably from 1% to 20%, most preferably from 2% to 10%, e.g. from 2.5% to 7%, e.g. about 4-5%, by weight of the liquid (or first) agrochemical (e.g. herbicidal) composition (e.g. EC).

The liquid (or first) agrochemical (preferably herbicidal) pinoxaden-containing compositions (e.g. EC compositions) according to, or used in, the first, second, third and/or fourth aspects of the present invention are preferably stable with respect to pinoxaden chemical stability. The pinoxaden chemical stability is preferably as follows:

Preferably, the liquid (or first) agrochemical (preferably herbicidal) compositions (e.g. EC compositions) are characterized by a breakdown (loss) of no more than 5 weight % (preferably no more than 4 weight %, more preferably less than 2.5% which typically means less than 2.5 weight %) of the pinoxaden after 2 weeks storage at a temperature of 50° C.

Alternatively or additionally, preferably, the liquid (or first) agrochemical (preferably herbicidal) compositions (e.g. EC compositions) are characterized by a breakdown (loss) of no more than 5 weight % (preferably no more than 4 weight %, more preferably no more than 3 weight %) of the pinoxaden after 2 weeks storage at a temperature of 54° C.

Alternatively or additionally, preferably, the liquid (or first) agrochemical (preferably herbicidal) compositions (e.g. EC compositions) are characterized by a breakdown (loss) of no more than 4 weight % (preferably no more than 3 weight %, more preferably no more than 2.5 weight %) of the pinoxaden after 8 weeks storage at a temperature of 38° C.

Alternatively or additionally, preferably, the liquid (or first) agrochemical (preferably herbicidal) compositions (e.g. EC compositions) are characterized by a breakdown (loss) of no more than 13 weight % (preferably no more than 11 weight %, more preferably no more than 9 weight %) of the pinoxaden after 8 weeks storage at a temperature of 50° C.

Preferably, in particular for maximum pinoxaden chemical stability, e.g. when an alcohol solvent is present, the composition (in particular the liquid (or first) agrochemical (preferably herbicidal) composition, typically in the form of an EC) contains substantially no (e.g. less than 0.1% w/w of, e.g. less than 0.01% w/w of, e.g. less than 0.001% w/w of, e.g. 0% of) acidic ingredient(s) which has/have a pKa of 4.0 or less or 3.5 or less (in particular 3.0 or less, e.g. 2.0 or less) when measured in water at 20 to 26° C. (more preferably at 25±1° C.).

Preferably, in particular for maximum pinoxaden chemical stability, e.g. when an alcohol solvent is present, the composition (in particular the liquid (or first) agrochemical (preferably herbicidal) composition, typically in the form of an EC) contains substantially no (e.g. less than 0.1% w/w of, e.g. less than 0.01% w/w of, e.g. less than 0.001% w/w of, e.g. 0% of) strongly basic ingredient(s) whose conjugate acid(s) has/have a pKa of 10 or more, or 9 or more, or 8 or more, when measured in water at 20 to 26° C. (more preferably at 25±1° C.).

Preferably, in particular for maximum pinoxaden chemical stability, the liquid (or first) agrochemical (preferably herbicidal) composition, e.g. in the form of an emulsifiable concentrate (EC), contains substantially no water (in particular less than 1% w/w of water, more particularly less than 0.5% w/w, e.g. equal to or less than 0.2% w/w of water).

Surfactants/Emulsifiers

In the second aspect of the invention, and preferably in the first, third and/or fourth aspects of the invention, the liquid (or first) agrochemical (preferably herbicidal) composition comprises:

(d) a surfactant system comprising (in particular consisting essentially of, e.g. being):

(d1) a butanol [ethylene oxide (EO)-propylene oxide (PO)] copolymer;

(d2) castor oil ethoxylate (preferably having from 20-50 EO, e.g. from 30-44 EO); and (d3) a block copolymer of ethylene oxide (EO) and propylene oxide (PO).

For component (d1), preferably the butanol [ethylene oxide (EO)-propylene oxide (PO)] copolymer is present in from 2% to 10%, preferably from 3% to 6% or from 3% to 5%, e.g. from 4 to 5%, by weight of the liquid (or first) agrochemical (e.g. herbicidal) composition (e.g. EC).

Preferably, the butanol [ethylene oxide (EO)-propylene oxide (PO)] copolymer is defined by a PO of 47-51%, and a EO of 49-53%, by weight of the EO and PO present.

Preferably, the butanol EO/PO copolymer comprises ATLAS™ G-5004LD (e.g. available from Croda Chocques SAS or Croda International plc), or Toximul™ 8320 LM (e.g. available from Stepan Company).

For component (d3), preferably the block copolymer of ethylene oxide (EO) and propylene oxide (PO) is present in from 0.5% to 8% or from 1% to 7%, preferably from 1% to 5%, e.g. from 2% to 4%, by weight of the liquid (or first) agrochemical (e.g. herbicidal) composition (e.g. EC).

For component (d3), preferably, the block copolymer of ethylene oxide (EO) and propylene oxide (PO) is defined by a PO of 40-75% (e.g. 50-70% or 55-65%, preferably about 60%), and a EO of 25-60% (e.g. 30-50% or 35-45%, preferably about 40%), by weight of the total EO and PO present.

For component (d3), preferably the block copolymer of ethylene oxide (EO) and propylene oxide (PO) comprises Synperonic™ PE/L 64, typically available from Croda Chocques SAS or Croda International plc. Synperonic™ PE/L 64 is believed to be poloxamer 184, and/or is according to or within CAS no. 9003-11-6 and/or CAS no. 106392-12-5.

For component (d2), preferably the castor oil ethoxylate (preferably having from 20-50 EO, e.g. from 30-44 EO) is present in from 0.5% to 7.5% or from 1% to 6% or from 1% to 5%, preferably from 1% to 3%, e.g. from 1.5 to 2%, by weight of the liquid (or first) agrochemical (e.g. herbicidal) composition (e.g. EC).

Preferably, in all aspects of the invention, the liquid (or first) agrochemical e.g. herbicidal composition contains an emulsifier and/or surfactant which is a castor oil-alkylene oxide addition product (condensation product), more preferably castor oil ethoxylate (preferably having 20 to 50 EO, more preferably 30-44 EO; i.e. containing and/or produced using 20 to 50 (preferably 30-44) moles of ethylene oxide (EO) per mole of castor oil). The castor oil-alkylene oxide addition product is typically present in from 1.5% to 10%, preferably from 2.5% to 7.5%, more preferably from 3% to 5%, by weight of the liquid (or first) agrochemical e.g. herbicidal composition (e.g. EC).

More preferably, in all aspects of the invention, the liquid (or first) agrochemical e.g. herbicidal composition contains an emulsifier and/or surfactant which is:

(i) Alkamuls EL-620/LI™ castor oil ethoxylate (which typically has about 30 EO), typically commercially available from Rhodia (e.g. Cranbury, N.J., USA; or Aubervilliers Cedex, France; or Sao Paulo, Brazil; or Singapore); and/or (ii) Servirox OEG 59 E™ castor oil ethoxylate (which typically has about 30-44 EO, or, for example, about 31 EO), typically commercially available from Elementis Specialties (e.g. Langestraat 167, 7491 A E Delden, The Netherlands), or Sasol Servo B V, or Brenntag N V (Belgium); and/or (iii) Servirox OEG 45™ castor oil ethoxylate.

Preferably, in all aspects of the invention, the liquid (or first) herbicidal composition of, or used in, the invention, especially for an emulsifiable concentrate, preferably comprises one or more emulsifiers and/or surfactants.

Preferably, the one or more emulsifiers and/or surfactants comprise: a salt (e.g. an alkaline earth metal salt, e.g. a calcium salt) of a $C_1$-$C_{22}$alkyl-phenyl-sulfonate (e.g. a salt of a $C_8$-$C_{18}$alkyl-phenyksulfonate), such as calcium dodecylbenzenesulfonate (e.g. linear); a castor oil-alkylene oxide addition product (condensation product) (note: castor oil contains a triglyceride in which most of the fatty acid chains are ricinoleic acid which includes an OH group), in particular castor oil ethoxylate which can for example have varying amounts of ethoxylation, e.g. a castor oil ethoxylate (20 to 50 EO) (i.e. containing and/or produced using 20 to 50 moles of ethylene oxide (EO) per mole of castor oil) or preferably castor oil ethoxylate (30-44 EO); an alcohol-alkylene oxide addition product (condensation product), in particular a $C_1$-$C_{22}$alcohol-alkylene oxide addition product, such as a $C_8$-$C_{22}$alcohol ethoxylate (which can e.g. have varying amounts of ethoxylation) such as tridecyl alcohol ethoxylate; an alkylphenol-alkylene oxide addition product (condensation product), such as nonylphenol ethoxylate; a di$C_1$-$C_{22}$alkyl ester of a sulfosuccinate salt, such as sodium di(2-ethylhexyl)sulfosuccinate; a sorbitol ester, such as sorbitol oleate; a polyethylene glycol ester of a $C_8$-$C_{22}$fatty acid, such as polyethylene glycol stearate; a block copolymer of ethylene oxide (EO) and propylene oxide (PO); a butanol ethylene oxide (EO)/propylene oxide (PO) copolymer [i.e. or e.g. methyloxirane, polymer with oxirane, monobutyl ether], such as Atlas G-5000D™ butanol EO/PO copolymer (e.g. available from Croda); or a salt of a mono- and/or di-alkyl phosphate ester; or a mixture of two or more of these emulsifiers. Alternatively or additionally, one or more other emulsifiers can be used, preferably a tristyrylphenol alkoxylate such as a tristyrylphenol ethoxylate and/or a tristyrylphenol ethoxylate-propoxylate, more particularly a tristyrylphenol ethoxylate containing 8 to 30 (preferably 10 to 25) moles of ethylene oxide (EO) per mole of tristyrylphenol, such as Soprophor TS/10™ (10 moles EO), Soprophor BSU™ (16 moles EO), or Soprophor S/25™ (25 moles EO), all Soprophor™ tristyrylphenol alkoxylates being available from Rhodia, at 40 Rue de la Haie-Coq, 93306 Aubervilliers Cedex, France, and/or at Cranbury, N.J., USA); and/or one or more other emulsifier(s) as described e.g. in "McCutcheon's Detergents and Emulsifiers Annual", MC Publishing Corp., Ridgewood, N.J., 1981. A mixture of two or more of any of these emulsifiers can also be used.

Typically, the one or more emulsifiers and/or surfactants are present in a total of from 0.5% to 35%, preferably from 1% to 20% or from 2% to 20%, more preferably from 2% to 10%, still more preferably from 3% to 8%, by weight of the liquid (or first) agrochemical e.g. herbicidal composition (e.g. EC).

Optionally, the liquid (or first) agrochemical e.g. herbicidal composition contains an emulsifier and/or surfactants which is a salt (e.g. an alkaline earth metal salt, in particular a calcium salt) of a $C_1$-$C_{22}$alkyl-phenyl-sulfonate, preferably a salt (e.g. an alkaline earth metal salt, in particular a calcium salt) of a $C_8$-$C_{18}$alkyl-phenyl-sulfonate, most preferably calcium dodecyl-benzenesulfonate (e.g. linear); the salt of the $C_1$-$C_{22}$alkyl-phenyl-sulfonate is typically present in from 0.5% to 7.5%, preferably from 1% to 5%, more preferably from 2% to 3%, by weight of the liquid (or first) agrochemical e.g. herbicidal composition (e.g. EC). More preferably, the liquid (or first) agrochemical e.g. herbicidal composition contains an emulsifier which is: Rhodocal 60/BE™ calcium dodecylbenzenesulfonate (linear) (which typically has an about 60% content of active ingredient; typically commercially available from Rhodia (Cranbury, N.J., USA; or Aubervilliers Cedex, France; or Sao Paulo, Brazil; or Singapore)), or Nansa EVM63/B™ calcium dodecylbenzenesulfonate (linear); preferably Rhodocal 60/BE™.

Preferably, the liquid (or first) agrochemical e.g. herbicidal composition contains an emulsifier and/or surfactant which is a castor oil-alkylene oxide addition product (condensation product), more preferably castor oil ethoxylate (preferably having 20 to 50 EO, more preferably 30-44 EO; i.e. containing and/or produced using 20 to 50 (preferably 30-44) moles of ethylene oxide (EO) per mole of castor oil). The castor oil-alkylene oxide addition product is typically present in from 1.5% to 10%, preferably from 2.5% to 7.5%, more preferably from 3% to 5%, by weight of the liquid (or first) agrochemical e.g. herbicidal composition (e.g. EC). More preferably, additionally or alternatively, the liquid (or first) agrochemical e.g. herbicidal composition contains an emulsifier which is:

(i) Alkamuls EL-620/LI™ castor oil ethoxylate (which typically has about 30 EO), typically commercially available from Rhodia (e.g. Cranbury, N.J., USA; or Aubervilliers Cedex, France; or Sao Paulo, Brazil; or Singapore); or (ii) Servirox OEG 59 E™ castor oil ethoxylate (which typically has about 30-44 EO, or, more specifically, about 31 EO), typically commercially available from Elementis Specialties (e.g. Langestraat 167, 7491 A E Delden, The Netherlands), or Sasol Servo B V, or Brenntag N V (Belgium); or (iii) Servirox OEG 45™ castor oil ethoxylate.

Other Ingredients

The agrochemical e.g. herbicidal compositions of, or used in, the invention can optionally comprise one or more additional formulation aids known in the art such as: crystallisation inhibitors, suspending agents, dyes, anti-oxidants, foaming agents, light absorbers, mixing aids, anti-foams, complexing agents, neutralising or pH-modifying substances and buffers, corrosion-inhibitors, fragrances, wetting agents, absorption improvers, micronutrients, plasticisers, glidants, lubricants, dispersants, anti-freezes, and/or microbiocides.

Composition Types

Preferably, the liquid (or first) agrochemical e.g. herbicidal composition according to, or used in, the present invention is in the form of an emulsifiable concentrate (EC), an oil dispersion (OD), a dispersible concentrate (DC), a suspo-emulsion (SE), or a microemulsifiable concentrate; in particular an emulsifiable concentrate (EC), an oil dispersion (OD), or a dispersible concentrate (DC). However, it is also possible, though less preferable (e.g. for pinoxaden-containing compositions), that the composition is present in the form of a gel, an emulsion in water (EW) such as an oil-in-water emulsion, an oil flowable (a spreading oil), an aqueous dispersion or a capsule suspension, or in another liquid form e.g. such as those known, for example, from the Manual on Development and Use of FAO Specifications for Plant Protection Products, 5th Edition, 1999; from this second set of composition types, an emulsion in water (EW), such as an oil-in-water emulsion, is the most notable composition type, with an aqueous dispersion also being a notable composition type.

Most preferably, the liquid (or first) agrochemical e.g. herbicidal composition according to, or used in, the present invention is in the form of an emulsifiable concentrate (EC).

The liquid (or first) agrochemical e.g. herbicidal composition can either be applied, e.g. to the weeds and/or to the locus thereof e.g. the field, directly or more usually can be diluted prior to use, e.g. by diluting with an agriculturally-acceptable aqueous solvent (such as water) which is suitable for spraying onto a field. A diluted, typically aqueous, agrochemical e.g. herbicidal composition can be prepared, for example, by mixing (e.g. tank-mixing) with water, a liquid fertiliser, a micronutrient, a biological organism, an oil and/or or another solvent; in particular by mixing (e.g. tank-mixing) with water.

The formulations (compositions) can be prepared, for example, by mixing the active ingredients (e.g. the pinoxaden, and preferably also a safener) with the "inert" (i.e. not herbicidally active, preferably not agrochemically active) formulation ingredients, in order to obtain compositions e.g. in the form of concentrates, solutions, dispersions and/or emulsions.

Methods of Herbicidal Use

Another aspect of the invention (when one or more herbicides are used in the composition) provides a method for controlling and/or inhibiting the growth of weeds (in particular dicotyledonous and/or broadleaf weeds), comprising applying a liquid agrochemical (preferably herbicidal) composition, according to or as described or used in any aspect of the present invention (e.g. a herbicidally effective amount thereof), to the weeds or to the locus thereof, at a time after emergence of the weeds.

In all aspects of the invention, the weeds to be controlled and/or growth-inhibited may be monocotyledonous (preferably grassy) weeds, and/or dicotyledonous and/or broadleaf weeds.

In all aspects of the invention, monocotyledonous (preferably grassy) weeds, e.g. to be controlled and/or growth-inhibited (e.g. by the pinoxaden), typically comprise (e.g. are) weeds from the genus *Alopecurus, Apera, Avena, Echinochloa, Lolium, Phalaris* and/or *Setaria*; in particular: *Alopecurus myosuroides* (English name "blackgrass"), *Avena fatua* (English name "wild oats"), *Avena sativa* (English name "oats" (volunteer)), *Echinochloa crus-galli* (English name "common barnyard grass"), *Lolium perenne* (English name "perennial ryegrass"), *Lolium multiflorum* (English name "Italian ryegrass"), *Lolium persicum* (English name "Persian darnel"), *Lolium rigidum, Setaria viridis* (English name "green foxtail"), *Setaria faberi* (English name "giant foxtail") and/or *Setaria lutescens* (English name "yellow foxtail"). In non-oat cereal crops such as wheat and/or barley, control and/or growth inhibition of weeds from the genus *Alopecurus, Apera, Avena*, especially *Avena fatua, Lolium*, and/or *Setaria* is preferred; in particular *Avena* (especially *Avena fatua*) and/or *Setaria* (especially *Setaria viridis, Setaria lutescens* and/or *Setaria faberi*), e.g. in the US and/or Canada. The grassy weeds can alternatively or additionally comprise weeds from the genus *Panicum* such as *Panicum miliaceum* (English name "wild proso millet").

In all aspects of the invention, dicotyledonous and/or broadleaf weeds, e.g. to be controlled and/or growth-inhibited (e.g. by the fluroxypyr ester), in particular comprise (e.g. are) weeds from the genus *Kochia, Polygonum, Fallopia, Salsola, Descurainia, Helianthus, Lactuca, Solanum, Sinapsis, Amaranthus, Brassica, Chenopodium, Fagopyrum, Eriogonum, Convolvulus, Chrysanthemum, Cirsium, Matricaria, Galium* (e.g. *Galium aparine*, English name "catchweed bedstraw"), *Papaver, Stellaria, Viola* and/or *Veronica*; and/or can in particular comprise (e.g. be) weeds from the genus *Xanthium* (e.g. *Xanthium strumarium*, English name "common cocklebur"), *Linum* (e.g. *Linum usitatissimum*, English name "volunteer flax"), and/or *Ambrosia* (e.g. *Ambrosia artemisiifolia*, English name "common ragweed").

In all aspects (e.g. in the methods) of the present invention, the agrochemical (preferably herbicidal) compositions (e.g. liquid agrochemical e.g. herbicidal compositions) according to, or used in, the present invention are typically applied to crops of useful plants.

Crops of useful plants, on which the agrochemical (preferably herbicidal) compositions according to, or used in, the invention can be applied, include preferably non-oat cereals, in particular wheat (e.g. winter wheat, or spring wheat (also named summer wheat), or durum), barley (e.g. winter barley, or spring barley (also named summer barley)), triticale, and/or rye (e.g. winter rye).

The term "crops" is to be understood as also including crops that have been rendered tolerant to herbicides or classes of herbicides (for example ALS, GS, EPSPS, PPO and HPPD inhibitors) as a result of conventional methods of breeding or genetic engineering. An example of a crop that has been rendered tolerant e.g. to imidazolinones, such as imazamox, by conventional methods of breeding is Clearfield® summer rape (Canola). Examples of crops that have been rendered tolerant to herbicides by genetic engineering methods include e.g. glyphosate- and glufosinate-resistant maize varieties commercially available under the trade names RoundupReady® and LibertyLink®. Crops are also to be understood as being those which have been rendered resistant to harmful insects by genetic engineering methods, for example Bt maize (resistant to European corn borer), Bt cotton (resistant to cotton boll weevil) and also Bt potatoes (resistant to Colorado beetle). Examples of Bt maize are the Bt-176 maize hybrids of NK® (Syngenta Seeds). The Bt toxin is a protein that is formed naturally by *Bacillus thuringiensis* soil bacteria. Examples of toxins and transgenic plants able to synthesise such toxins are described in EP-A-451 878, EP-A-374 753, WO 93/07278, WO 95/34656, WO 03/052073 and EP-A-427 529. Examples of transgenic plants that contain one or more genes which code for an insecticidal resistance and express one or more toxins are KnockOut® (maize), Yield Gard® (maize), NuCOTIN33BC (cotton), Bollgard® (cotton), NewLeaf® (potatoes), NatureGard® and Protexcta®. Plant crops and their seed material can be resistant to herbicides and at the same time also to insect feeding ("stacked" transgenic events). Seed can, for example, have the ability to express an insecticidally active Cry3 protein and at the same time be glyphosate-tolerant. The term "crops" is to be understood as also including crops obtained as a result of conventional methods of breeding or genetic engineering which contain so-called output traits (e.g. improved flavour, storage stability, nutritional content).

Areas under cultivation, and/or the locus of weeds, and/or fields, are to be understood as including land where crop plants are already growing as well as land intended for the cultivation of those crop plants.

In all aspects of the invention, preferably, the liquid agrochemical (preferably herbicidal) composition is applied, at a time after emergence of the weeds, at an application rate of from 15 to 90 g/ha or preferably from 30 to 60 g/ha (more preferably 45 to 60 g/ha, in particular 60 g/ha) of pinoxaden.

The following Examples illustrate the invention further but do not limit the invention.

FORMULATION EXAMPLE 1

Emulsifiable Concentrate Containing Pinoxaden, Cloquintocet-Mexyl, Hexylene Glycol, a Mixture of Heavy Aromatic Hydrocarbons, Degalan™ P26 Thickener, TEHP, and Three Non-Ionic Surfactants This is an emulsifiable concentrate (EC) formulation (composition) of the herbicide pinoxaden. Besides 50 g/l pinoxaden, the composition contains 12.5 g/l of the safener cloquintocet-mexyl, 340 g/l of tris(2-ethylhexyl)phosphate (TEHP) as a built in adjuvant, three non-ionic surfactants/emulsifiers, Degalan™ P26 thickener, and an alcoholic solvent and a heavy aromatic solvent. In this Formulation, hexylene glycol is used as the alcoholic solvent.

Formulation Composition for Formulation Example 1

The amounts in the following section are for a 4000 liter batch.

| Raw materials (trade name) | Raw materials (chemical name) (and function) | Content [% w/v] | Assay (minimum purity) [% w/w] | Mass [kg t.q.] |
|---|---|---|---|---|
| pinoxaden* (made by Syngenta) | 2,2-dimethyl-propionic acid 8-(2,6-diethyl-4-methyl-phenyl)-9-oxo-1,2,4,5-tetrahydro-9H-pyrazolo[1,2-d][1,4,5]oxadiazepin-7-yl ester (pinoxaden) (a herbicide) | 5 | 97.00 | 206.2 kg |
| cloquintocet-mexyl* (made by Syngenta) | 5-chloro-8-quinolyloxyacetic acid-1-methylhexylester (a safener) | 1.25 | 93.00 | 53.8 kg |
| ATLAS ™ G-5004LD (e.g. available from Croda Chocques SAS) | butanol PO/EO copolymer (PO = propylene oxide; EO = ethylene oxide) (a non-ionic surfactant/emulsifier) | 5 | | 200 kg |
| SERVIROX ™ OEG 59 E (e.g. available from Elementis Specialties) | condensation product of castor oil and ethyleneoxide (castor oil ethoxylate) (30-44 EO) (a non-ionic surfactant/emulsifier) | 2 | | 80 kg |
| SYNPERONIC ™ PE/L 64 (e.g. available from Croda Chocques SAS) | block copolymer of oxirane and methyloxirane (block copolymer of ethylene oxide and propylene oxide) (a non-ionic surfactant/emulsifier) | 3 | | 120 kg |
| DEGALAN ™ P 26 (e.g. available from Evonik Röhm GmbH, Germany) | acrylic bead polymer based on isobutyl methacrylate (properties of DEGALAN ™ P 26: molecular weight 180000; glass transition temperature 66° C. (Tg) (DIN 53 765); viscosity number 55 cm$^3$/g (DIN 51 562); dynamic viscosity 150 mPa · s measured at 40% in methyl ethyl ketone) (a thickener) | 2.5% w/v (2.591% w/w) | | 100 kg |
| SYNERGEN ™ TEHP (e.g. available from Clariant GmbH, LANXESS Deutschland GmbH, Hangzhou Qianyang technology Co., Ltd) | tris(2-ethylhexyl) phosphate (a built-in adjuvant) | 34 | | 1360 kg |
| HEXYLENE GLYCOL (e.g. available from ARKEMA- France, Rhodia Geronazzo S.p.A) | 2-methyl-2,4-pentanediol (hexylene glycol) (an alcoholic solvent) | 19 | | 760 kg |
| SOLVESSO ™ 200 ND (e.g. available from DHC Solvent Chemie GmbH, ExxonMobil Chemical Central Europe GmbH, Exxon Chemical Company, Petrochem Carless Ltd.) | mixture of heavy aromatic hydrocarbons (naphthalene-depleted (ND)) (a heavy aromatic solvent) | to 100 | | 980 kg |
| Density of final formulation | 0.965 g/ml | 4000 liters batch volume | | 3860 kg batch weight |

*The amounts have to be adjusted according to the active ingredient content (% purity) of pinoxaden and cloquintocet-mexyl starting materials used.

Preparation Procedure for Formulation Example 1
Preparation of the 20 Weight % Degalan™ P 26 Thickener Premix Because Degalan™ P 26 is best dissolved in pure Solvesso™ (a mixture of heavy aromatic hydrocarbons), preferably a premix of Degalan™ P 26 is made dissolved in pure Solvesso™. This premix then can easily be mixed with the rest of the substances during the production of the emulsifiable concentrate formulation.

In order to produce the Degalan™ P 26 premix for a 4000 liter batch of emulsifiable concentrate the procedure is as follows:

Charge in a separate vessel 400 kg of SOLVESSO™ and start agitation. Then add 100 kg DEGALAN™ P 26. Heat up to 60° C. Agitate for 1 hour at 60° C. until a homogeneous solution is obtained. Afterwards, cool the premix to less than 25° C. under agitation for easier handling.

Preparation of the 20 Weight % Pinoxaden Premix

It is recommended, though not essential, to prepare a pinoxaden-containing premix in a separate vessel. The pinoxaden should be dissolved in a mix of 65 weight % hexylene glycol and 35 weight % Solvesso™ (a mixture of heavy aromatic hydrocarbons).

In order to produce a pinoxaden premix for a 4000 liter batch, starting from pinoxaden having a purity (content) of 97% w/w, follow the instructions below:

Charge in a separate vessel 534.5 kg of hexylene glycol and 286.2 kg of SOLVESSO™ and start agitation. Add 212.4 kg of pinoxaden and stir until a homogeneous solution is obtained.

Preparation of the Formulation without a Pinoxaden Premix

The following is the procedure for preparation of the formulation when not using a pinoxaden premix:

1) Charge the remaining quantity of SOLVESSO™ (i.e. that amount not used in the DEGALAN™ P 26 premix)
2) Start agitation
3) Add SYNERGEN™ TEHP
4) Add 20 weight % premix of DEGALAN™ P 26 (prepared as described hereinabove)
5) Stir for 5 minutes
6) Add HEXYLENE GLYCOL
7) Add molten ATLAS™ G-5004LD under agitation
8) Add pre-warmed SERVIROX™ OEG 59 E
9) Add SYNPERONIC™ PE/L 64
10) Agitate for 5 minutes
11) Add cloquintocet-mexyl as a melt and wait till it is completely dissolved in the formulation
12) Check the temperature of the formulation. It must not exceed 25° C.; cool if necessary
13) Agitate for 5 minutes
14) Add pinoxaden in powder form and continue stirring
15) Inertisation and stirring at less than 25° C. for 1 to 2 hours until all has dissolved
16) Filter the formulation without adding a filter aid through a GAF filter or similar with a pore size of less than 5 microns.

Preparation of the Formulation with a 20 Weight % Pinoxaden Premix

The following is the procedure for preparation of the formulation when using a 20 weight % pinoxaden premix (prepared as described hereinabove):

1) Charge the remaining quantity of SOLVESSO™ (i.e. that amount not used in the DEGALAN™ P 26 premix and not used in the pinoxaden premix)
2) Start agitation
3) Add SYNERGEN™ TEHP
4) Add 20 weight % premix of DEGALAN™ P 26 (prepared as described hereinabove)
5) Stir for 5 minutes
6) Add the remaining HEXYLENE GLYCOL (i.e. that amount not used in the pinoxaden premix)
7) Add molten ATLAS™ G-5004LD under agitation
8) Add the warm SERVIROX™ OEG 59 E
9) Add SYNPERONIC™ PE/L 64
10) Agitate for 5 minutes
11) Add cloquintocet-mexyl as a melt and wait till it is completely dissolved in the formulation
12) Check the temperature. It must not exceed 25° C.; cool if necessary
13) Agitate for 5 minutes
14) Add pinoxaden in the form of a 20 weight % premix (prepared as described hereinabove) and continue stirring
15) Inertisation and stirring at less than 25° C. for 1 to 2 hours until all has dissolved
16) Filter the formulation without adding a filter aid through a GAF filter or similar with a pore size of less than 5 microns.

General Procedures and Practices for Formulation Example 1

Check the equipment for moisture or residues of water. All equipment and piping has to be completely dry. Flush the whole equipment with nitrogen to protect the formulation from air moisture.

Check the analysis of ingredients to ensure that the specification for water is met.

Heat the Servirox™ OEG 59 E up to 30° C., to reduce viscosity and facilitate homogenization and discharge, before adding to the formulation. Homogenize drums by rolling if the whole drum cannot be used.

Heat the ATLAS™ G-5004LD up to 50° C. until it is molten, before adding to the formulation.

Heat the cloquintocet-mexyl up to 80° C. until it has melted and use it (add it to the formulation) within a few hours after it has become liquid.

After having added emulsifiers and cloquintocet-mexyl, check the temperature of the formulation batch. Avoid temperatures above 25° C. for the formulation, during the whole process. Do not heat the formulation to accelerate dissolution of pinoxaden. Filter the formulation below 25° C.; apply cooling if necessary.

Apparatus for Formulation Example 1

Vessels with agitators. Filter. Hold tank.

Water bath to pre-heat the SERVIROX™ OEG 59 E; and two hot cabinets to melt the cloquintocet-mexyl and the ATLAS™ G-5004LD.

Kinematic Viscosity of Formulation Example 1
Method for Measuring Kinematic Viscosity A typical method for measuring the kinematic viscosity, e.g. of a or the liquid (or first) agrochemical (e.g. herbicidal) composition, is as follows. This method is and/or has been used by the patent applicant in the laboratory. A Rheoplus Physica™ MCR 301 rheometer (or viscosimeter) is used, which is available from Anton Paar. Approximately 80 mL (or, alternatively, approximately 19 mL) of the liquid (or first) agrochemical (e.g. herbicidal) composition is transferred to a or the cylinder of the viscosimeter (or rheometer). The spindle of the viscosimeter (or rheometer) is then submerged and the sample of the composition is heated up to 40° C. and kept at this temperature for 30 minutes. Then, the spindle starts rotation with gradually increasing speed (rotational speed or shear rate), starting from 0 $s^{-1}$ and gradually increasing to 300 $s^{-1}$ (preferably within 120 seconds); when the maximum rotation is reached the spindle slows down from 300 s$^{-1}$ to 0 s$^{-1}$ while measuring and documenting various measurement points of viscosity at different rotational speeds. After cooling down to 20° C. one can remove the sample of the composition. In such viscosity measurements, the measurement points show the dependency of the viscosity on the rotational speed (or shear rate) of the composition, at the tested temperature (here, 40° C.). The viscosimeter (or rheometer) determines the kinematic viscosity by dividing the absolute viscosity by the density of the fluid.

Results for Formulation Example 1

Using substantially the above measurement method (with or without minor variations thereof), the kinematic viscosity of Formulation Example 1 was found to be 24 mm$^2$/second at 40° C. (laboratory reference SMU9AL001).

Alternative Variation to Formulation Example 1

In an alternative, optional, variation of the above Formulation Example 1:

ingredient Atlas™ G-5004LD (e.g. available from Croda Chocques SAS) can be optionally be replaced by the same amount of Toximul™ 8320 LM (e.g. available from Stepan Company); and/or Servirox™ OEG 59 E (e.g. available from Elementis Specialties or Sasol Servo BV) can optionally be replaced by Alkamuls™ EL-620/LI (e.g. available from Rhodia, Inc., USA, or Rhodia in FR, BR or SG); and/or Solvesso™ 200 ND can optionally be replaced by Caromax™ 28 LNS.

FORMULATION EXAMPLE 2

Emulsifiable Concentrate Containing Pinoxaden, Clodinafop-Propargyl, Cloquintocet-Mexyl, Hexylene Glycol, a Mixture of Heavy Aromatic Hydrocarbons, Degalan™ P26 Thickener, TEHP, and Three Non-Ionic Surfactants This is an emulsifiable concentrate (EC) formulation (composition) of the herbicides pinoxaden and clodinafop-propargyl. Besides 25 g/l pinoxaden and 25 g/l clodinafop-propargyl, the formulation contains 6.25 g/l of the safener cloquintocet-mexyl, 340 g/L of tris(2-ethylhexyl)phosphate (TEHP) as a built in adjuvant, three non-ionic surfactants/emulsifiers, Degalan™ P26 thickener, and an alcoholic solvent and a heavy aromatic solvent. In this Formulation, hexylene glycol is used as the alcoholic solvent.

Formulation Composition for Formulation Example 2

The amounts in the following section are for a 4000 liter batch.

| Raw materials (trade name) | Raw materials (chemical name) (and function) | Content [% w/v] | Assay (minimum purity) [% w/w] | Mass [kg t.q.] |
|---|---|---|---|---|
| pinoxaden* (made by Syngenta) | 2,2-dimethyl-propionic acid 8-(2,6-diethyl-4-methyl-phenyl)-9-oxo-1,2,4,5-tetrahydro-9H-pyrazolo[1,2-d][1,4,5]oxadiazepin-7-yl ester (a herbicide) | 2.5 | 97.00 | 103.2 kg |
| clodinafop-propargyl* | 2-propynyl (R)-2-[4-(5-chloro-3-fluoro-2-pyridinyloxy)-phenoxy]-propionate (a herbicide) | 2.5 | 96.00 | 104.2 kg |
| cloquintocet-mexyl* (made by Syngenta) | 5-chloro-8-quinolyloxyacetic acid-1-methylhexylester (a safener) | 0.625 | 93.00 | 26.9 kg |
| ATLAS ™ G-5004LD (e.g. available from Croda Chocques SAS) | butanol PO/EO copolymer (PO = propylene oxide; EO = ethylene oxide) (a non-ionic surfactant/emulsifier) | 5 | | 200 kg |
| SERVIROX ™ OEG 59 E (e.g. available from Elementis Specialties) | condensation product of castor oil and ethylene oxide (castor oil ethoxylate) (30-44 EO) (a non-ionic surfactant/emulsifier) | 2 | | 80 kg |
| SYNPERONIC ™ PE/L 64 (e.g. available from Croda Chocques SAS) | block copolymer of oxirane and methyloxirane (block copolymer of ethylene oxide and propylene oxide) (a non-ionic surfactant/emulsifier) | 3 | | 120 kg |
| DEGALAN ™ P 26 (e.g. available from Evonik Röhm GmbH, Germany) | acrylic bead polymer based on isobutyl methacrylate (properties of DEGALAN ™ P 26: molecular weight 180000; glass transition temperature 66° C. (Tg) (DIN 53 765); viscosity number 55 cm$^3$/g (DIN 51 562); dynamic viscosity 150 mPa · s measured at 40% in methyl ethyl ketone) (a thickener) | 2.5% w/v (2.591% w/w) | | 100 kg |
| SYNERGEN ™ TEHP (e.g. available from Clariant GmbH, LANXESS Deutschland GmbH, Hangzhou Qianyang technology Co., Ltd) | tris(2-ethylhexyl) phosphate (a built-in adjuvant) | 34 | | 1360 kg |

| Raw materials (trade name) | Raw materials (chemical name) (and function) | Content [% w/v] | Assay (minimum purity) [% w/w] | Mass [kg t.q.] |
|---|---|---|---|---|
| HEXYLENE GLYCOL (e.g. available from ARKEMA- France, Rhodia Geronazzo S.p.A) | 2-methyl-2,4-pentanediol (hexylene glycol) (an alcoholic solvent) | 19 | | 760 kg |
| SOLVESSO ™ 200 ND (e.g. available from DHC Solvent Chemie GmbH, ExxonMobil Chemical Central Europe GmbH, Exxon Chemical Company Petrochem Carless Ltd.) | mixture of heavy aromatic hydrocarbons (naphthalene-depleted (ND)) (a heavy aromatic solvent) | to 100 | | 1005.8 kg |
| Density of final formulation | 0.965 g/ml | | 4000 liters batch volume | 3860 kg batch weight |

*The amounts have to be adjusted according to the active ingredient (AI) content (% purity) of pinoxaden, clodinafop-propargyl and cloquintocet-mexyl starting materials used.

Preparation Procedure for Formulation Example 2
Preparation of the 20 Weight % Degalan™ P 26 Thickener Premix Degalan™ P 26 is best dissolved in pure Solvesso™ (a mixture of heavy aromatic hydrocarbons), therefore a premix of Degalan™ P 26 is preferably made, to avoid problems such as solidification of particles and incomplete dissolution. This premix then can easily be mixed with the rest of the substances during the production of the formulation.

In order to produce the Degalan™ P 26 premix for a 4000 liter batch, charge in a separate vessel 400 kg of SOLVESSO™ and start agitation. Then add 100 kg DEGALAN™ P 26. Heat up to 60° C. Agitate for 1 hour at 60° C. until a homogeneous solution is obtained. Afterwards, cool the premix to <25° C. under agitation for easier handling.

Preparation of the 20 Weight % Pinoxaden Premix

It is recommended to make a premix of pinoxaden in hexylene glycol and Solvesso™ (a mixture of heavy aromatic hydrocarbons). The pinoxaden should be dissolved in a mix of 65 weight % hexylene glycol and 35 weight % Solvesso™ (a mixture of heavy aromatic hydrocarbons).

In order to produce pinoxaden premix for a 4000 liter batch, follow the instructions below: Charge in a separate vessel 265.7 kg of hexylene glycol and 143.1 kg of SOLVESSO™ and start agitation. Add 106.2 kg of pinoxaden and stir until a homogeneous solution is obtained.

Preparation of the Formulation without a Pinoxaden Premix

This process should be used in the event that a pinoxaden premix is not prepared.

1) Charge the remaining quantity of SOLVESSO™ (i.e. that amount not used in the DEGALAN™ P 26 premix)
2) Start agitation
3) Add SYNERGEN™ TEHP
4) Add 20 weight % premix of DEGALAN™ P 26 (prepared as described hereinabove)
5) Stir for 5 minutes
6) Add HEXYLENE GLYCOL
7) Add the molten ATLAS™ G-5004LD under agitation
8) Add the warm SERVIROX™ OEG 59 E
9) Add SYNPERONIC™ PE/L 64
10) Add clodinafop-propargyl
11) Agitate for 5 minutes
12) Add cloquintocet-mexyl as a melt and wait till it is completely dissolved.
13) Check the temperature. It must not exceed 25° C.; cool if necessary
14) Agitate for 5 minutes
15) Add pinoxaden in powder form and continue stirring
16) Inertisation and Stirring at less than 25° C. for 1 to 2 hours until all has dissolved
17) Filter the formulation without adding a filter aid through a GAF filter or similar with a pore size of less than 5 microns.

Preparation of the Formulation with a 20 Weight % Pinoxaden Premix

This process should be used in the event that a pinoxaden premix (prepared as described hereinabove) is used.

1) Charge the remaining quantity of SOLVESSO™ (i.e. that amount not used in the DEGALAN™ P 26 premix and not used in the pinoxaden premix)
2) Start agitation
3) Add SYNERGEN™ TEHP
4) Add 20 weight % premix of DEGALAN™ P 26 (prepared as described hereinabove)
5) Stir for 5 minutes
6) Add the remaining quantity of HEXYLENE GLYCOL (i.e. that amount not used in the pinoxaden premix)
7) Add molten ATLAS™ G-5004LD under agitation
8) Add pre-warmed SERVIROX™ OEG 59 E
9) Add SYNPERONIC™ PE/L 64
10) Add clodinafop-propargyl
11) Agitate for 5 minutes
12) Add cloquintocet-mexyl as a melt and wait till it is completely dissolved.
13) Check the temperature. It must not exceed 25° C.; cool if necessary
14) Agitate for 5 minutes
15) Add pinoxaden in the form of a 20 weight % premix (prepared as described hereinabove) and continue stirring
16) Inertisation and Stirring at less than 25° C. for 1 to 2 hours until all has dissolved
17) Filter the formulation without adding a filter aid through a GAF filter or similar with a pore size of less than 5 microns.

General Procedures and Practices for Formulation Example 2

Check the equipment for moisture or residues of water. All equipment and piping has to be completely dry. Flush the whole equipment with nitrogen to protect the formulation from air moisture.

Heat the Servirox™ OEG 59 E up to 30° C. to reduce viscosity and facilitate homogenization and discharge. Homogenize drums by rolling if the whole drum cannot be used.

Heat the ATLAS™ G-5004LD up to 50° C. until it is molten.

Heat the cloquintocet-mexyl up to 80° C. until it has melted and use it in (add it to) the formulation within a few hours after it has become liquid.

After having added emulsifiers and cloquintocet-mexyl check the temperature of the formulation batch. Avoid temperatures above 25° C. for the formulation, during the whole process. Do not heat the formulation to accelerate dissolution of pinoxaden. Filtering is required. Filter the formulation below 25° C.; apply cooling if necessary.
Apparatus for Formulation Example 2

Vessels with agitators. Filter. Hold tank.

Water bath to pre-heat the SERVIROX™ OEG 59 E; and two hot cabinets to melt the cloquintocet-mexyl and the ATLAS™ G-5004LD.
Kinematic Viscosity of Formulation Example 2

Using substantially the kinematic viscosity measurement method disclosed in Formulation Example 1 (with or without minor variations thereof; rheometer or viscosimeter used is from Anton Paar), the kinematic viscosity of Formulation Example 2 was found to be 23.3 mm$^2$/second at 40° C. (laboratory reference SMU9AL002).
Alternative Variation to Formulation Example 2

In an alternative, optional, variation of the above Formulation Example 2:

ingredient Atlas™ G-5004LD (e.g. available from Croda Chocques SAS) can be optionally be replaced by the same amount of Toximul™ 8320 LM (e.g. available from Stepan Company); and/or Servirox™ OEG 59 E (e.g. available from Elementis Specialties, or Sasol Servo BV) can optionally be replaced by Alkamuls™ EL-620/LI (e.g. available from Rhodia, Inc., USA, or Rhodia in FR, BR or SG); and/or Solvesso™ 200 ND can optionally be replaced by Caromax™ 28 LNS.

FORMULATION EXAMPLES 3 AND 4

Emulsifiable Concentrates Containing Pinoxaden (Plus, for Example 4, Clodinafop-Propargyl), Cloquintocet-Mexyl, Hexylene Glycol, a Mixture of Heavy Aromatic Hydrocarbons, Degalan™ P26 Thickener, TEHP, and Three Non-Ionic Surfactants Formulation Example 3 is an emulsifiable concentrate (EC) formulation (composition) of the herbicide pinoxaden. The composition contains 60 g/l pinoxaden, 15 g/l of the safener cloquintocet-mexyl, 320 g/l of tris(2-ethylhexyl) phosphate (TEHP) as a built in adjuvant, three non-ionic surfactants, 25 g/l of Degalan™ P26 thickener, 220 g/l of hexylene glycol as an alcoholic solvent, and a heavy aromatic hydrocarbon solvent.

Formulation Example 4 is an emulsifiable concentrate (EC) formulation (composition) of the herbicides pinoxaden and clodinafop-propargyl. The composition contains 30 g/l pinoxaden, 30 g/l clodinafop-propargyl, 7.5 g/l of the safener cloquintocet-mexyl, 340 g/l of tris(2-ethylhexyl) phosphate (TEHP) as a built in adjuvant, three non-ionic surfactants, 25 g/l of Degalan™ P26 thickener, 200 g/l of hexylene glycol as an alcoholic solvent, and a heavy aromatic hydrocarbon solvent.
Formulation Composition for Formulation Examples 3 and 4

| Raw materials (trade name) | Raw materials (chemical name) (and function) | Formulation Example 3: Content [% w/v] | Formulation Example 4: Content [% w/v] |
|---|---|---|---|
| pinoxaden* (made by Syngenta) | (a herbicide) | 6 | 3 |
| clodinafop-propargyl* | (a herbicide) | 0 | 3 |
| cloquintocet-mexyl* (made by Syngenta) | (a safener) | 1.5 | 0.75 |
| ATLAS ™ G-5004LD (e.g. available from Croda Chocques SAS); or TOXIMUL ™ 8320 LM (e.g. available from Stepan Company) | butanol PO/EO copolymer (PO = propylene oxide; EO = ethylene oxide) (a non-ionic surfactant/ emulsifier) | 5 | 5 |
| SERVIROX ™ OEG 59 E (e.g. available from Elementis Specialties); or ALKAMULS ™ EL-620/LI (e.g. available from Rhodia) | condensation product of castor oil and ethylene oxide (castor oil ethoxylate) (ca. 30-44 EO) (a non-ionic surfactant/ emulsifier) | 2 | 2 |
| SYNPERONIC ™ PE/L 64 (e.g. available from Croda Chocques SAS) | block copolymer of oxirane and methyloxirane (block copolymer of ethylene oxide and propylene oxide) (a non-ionic surfactant/ emulsifier) | 3 | 3 |
| DEGALAN ™ P 26 (e.g. available from Evonik Röhm GmbH, Germany) | acrylic bead polymer based on isobutyl methacrylate** (a thickener) | 2.5 | 2.5 |
| SYNERGEN ™ TEHP (e.g. available from Clariant GmbH, LANXESS Deutschland GmbH, or Hangzhou Qianyang technology Co. Ltd) | tris(2-ethylhexyl) phosphate (a built-in adjuvant) | 32 | 34 |
| HEXYLENE GLYCOL (e.g. available from ARKEMA-France, Rhodia Geronazzo S.p.A) | 2-methyl-2,4-pentanediol (hexylene glycol) (an alcoholic solvent) | 22 | 20 |

| Raw materials (trade name) | Raw materials (chemical name) (and function) | Formulation Example 3: Content [% w/v] | Formulation Example 4: Content [% w/v] |
|---|---|---|---|
| SOLVESSO ™ 200 ND (e.g. available from DHC Solvent Chemie GmbH, ExxonMobil Chemical Central Europe GmbH, Exxon Chemical Company, or Petrochem Carless Ltd.); or alternatively AROMATIC ™ 200 ND (eg from Exxon USA); or CAROMAX ™ 28 LNS; or HYDROSOL ™ A 230/290 Density of final formulation | mixture of heavy aromatic hydrocarbons (naphthalene-depleted (ND)) (a heavy aromatic solvent) | remainder (to 100%). Minimum 20% w/v; maximum 25% w/v. | remainder (to 100%) |

*The amounts have to be adjusted according to the active ingredient (AI) content (% purity) of pinoxaden, cloquintocet-mexyl, and (when present) clodinafop-propargyl starting materials used.
**The properties of DEGALAN ™ P 26 (an acrylic bead polymer based on isobutyl methacrylate) are: molecular weight 180000; glass transition temperature 66° C. (Tg) (DIN 53 765); viscosity number 55 cm³/g (DIN 51 562); dynamic viscosity 150 mPa · s measured at 40% in methyl ethyl ketone.

FORMULATION EXAMPLES 5 AND 6

Emulsifiable Concentrates Containing Pinoxaden, Florasulam (Plus, for Example 6, Clodinafop-Propargyl), Cloquintocet-Mexyl, 1,2-Propylene Carbonate, Benzyl Alcohol, a Mixture of Heavy Aromatic Hydrocarbons, 3.5% w/v Degalan™ P26 Thickener, TEHP, and Three Non-Ionic Surfactants Formulation Example 5 is an emulsifiable concentrate (EC) formulation (composition) of the herbicides pinoxaden and florasulam. The composition contains 45 g/l pinoxaden, 5 g/l florasulam, 11.25 g/l of the safener cloquintocet-mexyl, 340 g/l of tris(2-ethylhexyl)phosphate (TEHP) as a built in adjuvant, three non-ionic surfactants, 35 g/l of Degalan™ P26 thickener, 150 g/l of 1,2-propylene carbonate, 150 g/l of benzyl alcohol as an alcoholic solvent, and a heavy aromatic hydrocarbon solvent.

Formulation Example 6 is an emulsifiable concentrate (EC) formulation (composition) of the herbicides pinoxaden, clodinafop-propargyl and florasulam. The composition contains 30 g/l pinoxaden, 30 g/l clodinafop-propargyl, 7.5 g/l florasulam, 7.5 g/l of the safener cloquintocet-mexyl, 340 g/l of tris(2-ethylhexyl)phosphate (TEHP) as a built in adjuvant, three non-ionic surfactants, 35 g/l of Degalan™ P26 thickener, 150 g/l of 1,2-propylene carbonate, 150 g/l of benzyl alcohol as an alcoholic solvent, and a heavy aromatic hydrocarbon solvent.

Formulation Composition for Formulation Examples 5 and 6

| Raw materials (trade name) | Raw materials (chemical name) (and function) | Formulation Example 5: Content [% w/v] | Formulation Example 6: Content [% w/v] |
|---|---|---|---|
| pinoxaden* (made by Syngenta) | (a herbicide) | 4.5 | 3 |
| clodinafop-propargyl* | (a herbicide) | 0 | 3 |
| florasulam* | (a herbicide) | 0.5 | 0.75 |
| cloquintocet-mexyl* (made by Syngenta) | (a safener) | 1.125 | 0.75 |
| ATLAS ™ G-5004LD (e.g. available from Croda Chocques SAS); or TOXIMUL ™ 8320 LM (e.g. available from Stepan Company) | butanol PO/EO copolymer (PO = propylene oxide; EO = ethylene oxide) (a non-ionic surfactant/emulsifier) | 4 | 4 |
| SERVIROX ™ OEG 59 E (e.g. available from Elementis Specialties); or ALKAMULS ™ EL-620/LI (e.g. available from Rhodia) | condensation product of castor oil and ethylene oxide (castor oil ethoxylate) (ca. 30-44 EO) (a non-ionic surfactant/emulsifier) | 1.5 | 1.5 |
| SYNPERONIC ™ PE/L 64 (e.g. available from Croda Chocques SAS) | block copolymer of oxirane and methyloxirane (block copolymer of ethylene oxide and propylene oxide) (a non-ionic surfactant/emulsifier) | 2 | 2 |
| DEGALAN ™ P 26 (e.g. available from Evonik Röhm GmbH, Germany) | acrylic bead polymer based on isobutyl methacrylate** (a thickener) | 3.5 | 3.5 |
| SYNERGEN ™ TEHP (e.g. available from Clariant GmbH, LANXESS Deutsch-land GmbH, or Hangzhou Qianyang technology Co. Ltd) | tris(2-ethylhexyl) phosphate (a built-in adjuvant) | 34 | 34 |

-continued

| Raw materials (trade name) | Raw materials (chemical name) (and function) | Formulation Example 5: Content [% w/v] | Formulation Example 6: Content [% w/v] |
|---|---|---|---|
| 1,2-propylene carbonate | (a solvent) | 15 | 15 |
| benzyl alcohol | (an alcoholic solvent) | 15 | 15 |
| SOLVESSO™ 200 ND (e.g. available from DHC Solvent Chemie GmbH, ExxonMobil Chemical Central Europe GmbH, Exxon Chemical Company, or Petrochem Carless Ltd.); or, alternatively, AROMATIC™ 200 ND or NAPHTHALENE DEPLETED AROMATIC™ 200 FLUID (e.g. from Exxon, USA); or CAROMAX™ 28 LNS; or HYDROSOL™ A 230/290 | mixture of heavy aromatic hydrocarbons (naphthalene-depleted (ND)) (a heavy aromatic solvent) | remainder (to 100%) | remainder (to 100%) |
| Measured Density of final formulation at 23° C. | | 1.0153 g/ml at 23° C. | 1.0184 g/ml at 23° C. |

*The amounts have to be adjusted according to the active ingredient (AI) content (% purity) of pinoxaden, florasulam, cloquintocet-mexyl, and (when present) clodinafop-propargyl starting materials used.
**The properties of DEGALAN™ P 26 (an acrylic bead polymer based on isobutyl methacrylate) are: molecular weight 180000; glass transition temperature 66° C. (Tg) (DIN 53 765); viscosity number 55 cm³/g (DIN 51 562); dynamic viscosity 150 mPa · s measured at 40% in methyl ethyl ketone.

Kinematic Viscosity of Formulation Examples 5 and 6

Using substantially the kinematic viscosity measurement method disclosed in Formulation Example 1 (with or without minor variations thereof; rheometer or viscosimeter used is from Anton Paar), the kinematic viscosities of these Formulation Examples were found to be as follows. In each case, the viscosity was measured at 40° C., but the kinematic viscosity was then calculated based on the densities measured at 23° C. (not 40° C.):

Formulation Example 5—Kinematic viscosity 20.5 mm²/second at 40° C. (calculated based on measured density of 1.0153 g/ml at 23° C.) (laboratory reference SMU2JP001).

Formulation Example 6—Kinematic viscosity 20.4 mm²/second at 40° C. (calculated based on measured density of 1.0184 g/ml at 23° C.) (laboratory reference SMU2JP001).

FORMULATION EXAMPLES 7 AND 8

Emulsifiable Concentrates Containing Pinoxaden, Florasulam (Plus, for Example 8, Clodinafop-Propargyl), Cloquintocet-Mexyl, 1,2-Propylene Carbonate, Benzyl Alcohol, a Mixture of Heavy Aromatic Hydrocarbons, 4.25% w/v Degalan™ P26 Thickener, TEHP, and Three Non-Ionic Surfactants Formulation Example 7 is an emulsifiable concentrate (EC) formulation (composition) containing the herbicides pinoxaden and florasulam. The composition contains 45 g/l pinoxaden, 5 g/l florasulam, 11.25 g/l of the safener cloquintocet-mexyl, 340 g/l of tris(2-ethylhexyl)phosphate (TEHP) as a built-in adjuvant, three non-ionic surfactants, 42.5 g/l of Degalan™ P26 thickener, 150 g/l of 1,2-propylene carbonate, 150 g/l of benzyl alcohol as an alcoholic solvent, and a heavy aromatic hydrocarbon solvent.

Formulation Example 8 is an emulsifiable concentrate (EC) formulation (composition) containing the herbicides pinoxaden, clodinafop-propargyl and florasulam. The composition contains 30 g/l pinoxaden, 30 g/l clodinafop-propargyl, 7.5 g/l florasulam, 7.5 g/l of the safener cloquintocet-mexyl, 340 g/l of tris(2-ethylhexyl)phosphate (TEHP) as a built-in adjuvant, three non-ionic surfactants, 42.5 g/l of Degalan™ P26 thickener, 150 g/l of 1,2-propylene carbonate, 150 g/l of benzyl alcohol as an alcoholic solvent, and a heavy aromatic hydrocarbon solvent.

Formulation Composition for Formulation Examples 7 and 8

| Raw materials (trade name) | Raw materials (chemical name) (and function) | Formulation Example 7: Content [% w/v + w/w] | Formulation Example 8: Content [% w/v + w/w] |
|---|---|---|---|
| pinoxaden* (made by Syngenta) | (a herbicide) | 4.5% w/v (4.4335% w/w) | 3% w/v (2.9412% w/w) |
| clodinafop-propargyl* | (a herbicide) | 0 | 3% w/v (2.9412% w/w) |
| florasulam* | (a herbicide) | 0.5% w/v (0.4926% w/w) | 0.75% w/v (0.7353% w/w) |
| cloquintocet-mexyl* (made by Syngenta) | (a safener) | 1.125% w/v (1.1084% w/w) | 0.75% w/v (0.7353% w/w) |

-continued

| Raw materials (trade name) | Raw materials (chemical name) (and function) | Formulation Example 7: Content [% w/v + w/w] | Formulation Example 8: Content [% w/v + w/w] |
|---|---|---|---|
| TOXIMUL ™ 8320 LM (e.g. available from Stepan Company); or, alternatively, ATLAS ™ G-5004LD (e.g. available from Croda Chocques SAS) | butanol PO/EO copolymer (PO = propylene oxide; EO = ethylene oxide) (CAS no. 9038-95-3) (a non-ionic surfactant/ emulsifier) | 4% w/v (3.9409% w/w) | 4% w/v (3.9216% w/w) |
| SERVIROX ™ OEG 59 E (e.g. available from Elementis Specialties); or, alternatively, ALKAMULS ™ EL-620/LI (e.g. available from Rhodia) | condensation product of castor oil and ethylene oxide (castor oil ethoxylate) (ca. 30-44 EO) (CAS no. 61791-12-6) (a non-ionic surfactant/ emulsifier) | 1.5% w/v (1.4778% w/w) | 1.5% w/v (1.4706% w/w) |
| SYNPERONIC ™ PE/L 64 (e.g. available from Croda Chocques SAS) | block copolymer of oxirane and methyloxirane (block copolymer of ethylene oxide and propylene oxide) (CAS no. 106392-12-5) (a non-ionic surfactant/emulsifier) | 2% w/v (1.9704% w/w) | 2% w/v (1.9608% w/w) |
| DEGALAN ™ P 26 (e.g. available from Evonik Rohm GmbH, Germany) | acrylic bead polymer based on isobutyl methacrylate** (a thickener) | 4.25% w/v (4.1872% w/w) | 4.25% w/v (4.1667% w/w) |
| SYNERGEN ™ TEHP (e.g. available from Clariant GmbH, LANXESS Deutsch-land GmbH, or Hangzhou Qianyang technology Co. Ltd) | tris(2-ethylhexyl) phosphate (a built-in adjuvant) | 34% w/v (33.4975% w/w) | 34% w/v (33.3333% w/w) |
| 1,2-propylene carbonate | (a solvent) | 15% w/v (14.7783% w/w) | 15% w/v (14.7059% w/w) |
| benzyl alcohol | (an alcoholic solvent) | 15% w/v (14.7783% w/w) | 15% w/v (14.7059% w/w) |
| SOLVESSO ™ 200 ND*** (e.g. available from DHC Solvent Chemie GmbH, ExxonMobil Chemical Central Europe GmbH, Exxon Chemical Company, or Petrochem Carless Ltd.); or, alternatively: Aromatic ™ 200 ND or Aromatic ™ 200 Fluid (ND) or Naphthalene Depleted Aromatic ™ 200 Fluid (e.g. from Exxon, USA), or CAROMAX ™ 28 LNS, or HYDROSOL ™ A 230/290 | mixture of heavy aromatic hydrocarbons (naphthalene-depleted (ND)) (a heavy aromatic solvent) | remainder (to 100%) | remainder (to 100%) |
| Measured Density of final formulation at 23° C. | | 1.0155 g/ml at 23° C. | 1.022 g/ml at 23° C. |

*The amounts have to be adjusted according to the active ingredient (AI) content (% purity) of pinoxaden, forasulam, cloquintocet-mexyl, and (when present) clodinafop-propargyl starting materials used.
**The properties of DEGALAN ™ P 26 (an acrylic bead polymer based on isobutyl methacrylate) are: molecular weight 180000; glass transition temperature 66° C. (Tg) (DIN 53 765); viscosity number 55 cm³/g (DIN 51 562); dynamic viscosity 150 mPa · s measured at 40% in methyl ethyl ketone.
***Solvesso ™ 200 ND (available from Exxon, Europe) typically has a low percentage (e.g. ca. 0.5%) of (unsubstituted) naphthalene (ND = naphthalene depleted), and comprises also varying percentages of other (e.g. higher) aromatic hydrocarbons, and in particular typically comprises naphthalenes substituted by alkyl(s) wherein the alkyl(s) contain 1, 2, 3 or 4 or more (e.g. 1, 2 or 3) carbon atoms in total. By way of example only, certain batches of Solvesso 200 ND ™ have been measured by Syngenta (in 2010 or beforehand) as comprising, very approximately, the following ingredients: ca. 0.5% of naphthalene, ca. 14% to ca. 22% of 1-methyl-naphthalene, ca. 14% to ca. 32% of 2-methyl-naphthalene, ca. 21% to ca. 25% of $C_2$-naphthalene (i.e. molecule(s) containing naphthalene + two additional carbon atoms, e.g. ethyl-naphthalene and/or dimethyl-naphthalene), ca. 9% to ca. 17% of $C_3$-naphthalene, 0% to ca. 11% of ($C_4$ and/or higher)-naphthalene(s), ca. 0.05% to ca. 0.5% of biphenyl, 0% to ca. 5% of $C_4$-benzene, and 0% to ca. 3% of $C_5$-benzene; and typically these mentioned ingredients form ca. 75% to ca. 97% by weight of the Solvesso ™ 200 ND.

Kinematic Viscosity of Formulation Examples 7 and 8

Using substantially the kinematic viscosity measurement method disclosed in Formulation Example 1 (with or without minor variations thereof; rheometer or viscosimeter used is from Anton Paar), the kinematic viscosities of these Formulation Examples were found to be as follows. In each case, the viscosity was measured at 40° C., but the kinematic viscosity was then calculated based on the densities measured at 23° C. (not 40° C.):

Formulation Example 7—Kinematic viscosity 22.8 mm$^2$/second at 40° C. (calculated based on measured density of 1.0155 g/ml at 23° C.) (laboratory reference SMU3IL003).

Formulation Example 8—Kinematic viscosity 23.3 mm$^2$/second at 40° C. (calculated based on measured density of 1.022 g/ml at 23° C.) (laboratory reference SMU3IL003).

FORMULATION EXAMPLES 9, 10, 11 AND 12—AND KINEMATIC VISCOSITIES

Formulation Examples 9 and 10 are substantially the same as Formulation Examples 7 and 8 respectively, except that 3.75% w/v of DEGALAN™ P 26 thickener (acrylic bead polymer based on isobutyl methacrylate) was used instead of 4.25% w/v.

Formulation Examples 11 and 12 are substantially the same as Formulation Examples 7 and 8 respectively, except that 4.0% w/v of DEGALAN™ P 26 thickener (acrylic bead polymer based on isobutyl methacrylate) was used instead of 4.25% w/v.

Using substantially the kinematic viscosity measurement method disclosed in Formulation Example 1 (with or without minor variations thereof; rheometer or viscosimeter used is from Anton Paar), the kinematic viscosities of these Formulation Examples were found to be as shown below. In each case, the viscosity was measured at 40° C., but the kinematic viscosity was then calculated based on the densities measured at 23° C. (not 40° C.).

Formulation Example 9 (pinoxaden+florasulam+cloquintocet-mexyl+3.75% w/v of DEGALAN™ P 26 thickener+1,2-propylene carbonate+benzyl alcohol, and other ingredients)—Kinematic viscosities for two batches are respectively 21.7 and 20.4 mm$^2$/second at 40° C. (calculated based on measured densities for the 2 batches of respectively 1.0158 and 1.0151 g/ml at 23° C.) (laboratory references SMU3BL014 and SMU3HL001).

Formulation Example 11 (pinoxaden+florasulam+cloquintocet-mexyl+4.0% w/v of DEGALAN™ P 26 thickener+1,2-propylene carbonate+benzyl alcohol, and other ingredients)—Kinematic viscosities for two batches are respectively 22.5 and 21.7 mm$^2$/second at 40° C. (calculated based on measured densities for the 2 batches of respectively 1.0184 and 1.0153 g/ml at 23° C.) (laboratory references SMU2GL012 and SMU3IL002).

Formulation Example 10 (pinoxaden+clodinafop-propargyl+florasulam+cloquintocet-mexyl+3.75% w/v of DEGALAN™ P 26 thickener+1,2-propylene carbonate+benzyl alcohol, and other ingredients)—Kinematic viscosities for two batches are respectively 21.8 and 20.8 mm$^2$/second at 40° C. (calculated based on measured densities for the 2 batches of respectively 1.02144 and 1.02334 g/ml at 23° C.) (laboratory references SMU3DL004 and SMU3HL001).

Formulation Example 12 (pinoxaden+clodinafop-propargyl+florasulam+cloquintocet-mexyl+4.0% w/v of DEGALAN™ P 26 thickener+1,2-propylene carbonate+benzyl alcohol, and other ingredients)—Kinematic viscosity is 22.2 mm$^2$/second at 40° C. (calculated based on measured density of 1.0217 g/ml at 23° C.) (laboratory reference SMU3IL002).

FORMULATION EXAMPLE 13

Emulsifiable Concentrate Containing Pinoxaden, Bromoxynil Octanoate, Cloquintocet-Mexyl, Hexylene Glycol, a Mixture of Heavy Aromatic Hydrocarbons, 2% w/v Degalan™ P26 Thickener, TEHP, and Two Non-Ionic Surfactants

| Raw materials (trade name) | Raw materials (chemical name) (and function) | Formulation Example 13: Content [% w/v] |
|---|---|---|
| pinoxaden* (made by Syngenta) | (a herbicide) | 3 |
| bromoxynil octanoate* | (a herbicide) | 18 |
| cloquintocet-mexyl* (made by Syngenta) | (a safener) | 0.75 |
| ATLAS ™ G-5004LD (e.g. available from Croda Chocques SAS); or TOXIMUL ™ 8320 LM (e.g. available from Stepan Company) | butanol PO/EO copolymer (PO = propylene oxide; EO = ethylene oxide) (a non-ionic surfactant/emulsifier) | 5 |
| SYNPERONIC ™ PE/L 64 (e.g. available from Croda Chocques SAS) | block copolymer of oxirane and methyloxirane (block copolymer of ethylene oxide and propylene oxide) (a non-ionic surfactant/emulsifier) | 5 |
| DEGALAN ™ P 26 (e.g. available from Evonik Röhm GmbH, Germany) | acrylic bead polymer based on isobutyl methacrylate** (a thickener) | 2 |
| SYNERGEN ™ TEHP (e.g. available from Clariant GmbH, LANXESS Deutsch-land GmbH, or Hangzhou Qianyang technology Co. Ltd) | tris(2-ethylhexyl) phosphate (a built-in adjuvant) | 17 |
| HEXYLENE GLYCOL (e.g. available from ARKEMA-France, Rhodia Geronazzo S.p.A) | 2-methyl-2,4-pentanediol (hexylene glycol) (an alcoholic solvent) | 15 |
| SOLVESSO ™ 200 ND (e.g. available from DHC Solvent Chemie GmbH, ExxonMobil Chemical Central Europe GmbH, Exxon Chemical Company, or Petrochem Carless Ltd.); or, alternatively, AROMATIC ™ 200 ND (e.g. from Exxon, USA); or CAROMAX ™ 28 LNS; or HYDROSOL ™ A 230/290 Density of final formulation at 23° C. | mixture of heavy aromatic hydrocarbons (naphthalene-depleted (ND)) (a heavy aromatic solvent) | remainder (to 100%) |

*The amounts have to be adjusted according to the active ingredient (AI) content (% purity) of pinoxaden, bromoxynil octanoate, and cloquintocet-mexyl starting materials used.

REFERENCE FORMULATION EXAMPLE 14

Emulsifiable Concentrate (EC) Containing Inter Alia Pinoxaden, Tetrahydrofurfuryl Alcohol (THFA) as Alcohol Solvent, TEHP Adjuvant, Polystyrene as Thickener, and 1 Nonionic and 1 Anionic Surfactant Ingredients are: 5% w/v pinoxaden, 1.25% w/v cloquintocet-mexyl, 5% w/v of the condensation product of castor oil and ethylene oxide (i.e. castor oil ethoxylate) (present as SERVIROX™ OEG 59 E) (as non-ionic surfactant), 2% w/v of calcium dodecyl-benzene sulfonate (linear) (present as NANSA™ EVM63/B or SERMUL™ EA 88) (as anionic surfactant), 0.5% w/v polystyrene (present as STYRON™ 666 D CLEAR) (as thickener), 34% w/v of tris(2-ethylhexyl)phosphate ("TEHP", present as SYNERGEN™ TEHP) (as built-in adjuvant), 18% w/v (tetrahydro-furan-2-yl)-methanol (tetrahydrofurfuryl alcohol) (as alcohol solvent), and rest (to 100% w/v) is a mixture of heavy aromatic hydrocarbons (as solvent) (e.g. present as SOLVESSO™ 200 ND).

BIOLOGICAL EXAMPLE 1

Efficacy Field Tests on Formulation Example 1

The aim of these field tests was to confirm the performance of Formulation Example 1 at 0.6. 0.9 and 1.2 l/ha (equivalent to 60, 45 and 30 g/ha pinoxaden respectively), applied post-emergence (at growth stage BBCH 12-39 of the crop) against grass weeds (*Alopecurus myosuroides, Apera Spica-venti, Avena fatua, Avena* sp., *Avena sterilis, Lolium multiflorum, Lolium rigidum, Lolium* sp., *Phalaris brachystachys, Phalaris minor, Phalaris paradoxa* and/or *Phalaris* sp.), and to compare the performance of Formulation Example 1 (according to the first and second aspects of the present invention, which contains inter alia pinoxaden, hexylene glycol as the alcohol solvent, an isobutyl methacrylate polymer thickener, and three non-ionic surfactants) to the Reference Formulation Example 14 (which contains inter alia pinoxaden, tetrahydrofurfuryl alcohol as the alcohol solvent, polystyrene thickener, and one non-ionic and one anionic surfactant). These two formulations were tested in the field on a wide range of grass weed species throughout different European zones. The resulting data supports that the new Formulation Example 1 (according to the first and second aspects of the present invention) is substantially equivalent to Reference Formulation Example 14 in term of post-emergence herbicidal activity against the tested grass weeds.

Materials and Methods

Trials were conducted in Belgium, Germany, the Netherlands, France, Italy, Lithuania, Poland, Portugal and Spain. As a general rule, the trial layout was according to the randomized complete block design with three replicates per treatment. All normal crop husbandry measures were applied to the trials area, according to crop requirements and in accordance with good agricultural practice. Trials included a range of soil types and locations to determine crop tolerance and efficacy on a number of commercially grown varieties, under a range of conditions. All the trials were placed within regions where cereal crops are commonly grown and data are presented on grass weeds which are also indigenous to the area covered. Crop growth stages and infestation levels were recorded at the time of application using the appropriate BBCH codes. Weed growth at application is described on the basis of development stage. Crop growth stages are described using the standard BBCH scale. In all trials, efficacy was assessed according to EPPO guidelines (% visual biomass reduction compared to untreated check).

TABLE

Detailed information describing spring application in winter cereal crops

| | |
|---|---|
| Crop, stage | Winter wheat, post-emergence, up to BBCH 39 |
| | Winter barley, post-emergence, up to BBCH 39 |
| | Winter rye, post-emergence, up to BBCH 39 |
| | Triticale, post-emergence, up to BBCH 39 |
| | Durum, post-emergence, up to BBCH 39 |
| Application Rate | 1.2 l/ha Formulation Example 1 (a EC50) = 60 g pinoxaden/ha |
| | 0.9 l/ha Formulation Example 1 (a EC50) = 45 g pinoxaden/ha |
| | 0.6 l/ha Formulation Example 1 (a EC50) = 30 g pinoxaden/ha |
| Use frequency | 1x |
| Application timing | Post-emergence to weeds and crop, crop between BBCH 12-39 |
| Target weeds | Annual grass weeds |

Spring Application in Winter Cereals—Results

Data demonstrated that Formulation Example 1 at the rates of 0.6, 0.9 and 1.2 l/ha was equivalent to the efficacy of 0.6, 0.9 and 1.2 l/ha of Reference Formulation Example 14 against *Alopecurus myosuroides, Apera spica-venti, Avena fatua, Avena* sp., *Avena sterilis, Lolium multiflorum, Lolium rigidum, Lolium* sp., *Phalaris brachystachys, Phalaris paradoxa* and *Phalaris* sp.

TABLE

Grass weed control results summarized across all countries by 0.6, 0.9 and 1.2 l/ha of Formulation Example 1 and Reference Formulation Example 14 in spring application in winter cereals in the efficacy tests (spring last assessment evaluation of control as % visual biomass reduction compared to untreated check, N = number of trials).

| | | | Mean % control at a range of doses of Formulation Example 1 and Reference Formulation Example 14 | | | |
|---|---|---|---|---|---|---|
| | | | Example 1 [%] | | Ref. Example 14 [%] | |
| Target | N | Dose rate l/ha (%) | Mean | Min/max | Mean | Min/max |
| *Alopecurus* | 7 | 1.2 (100%) | 94.7 | 81.7/100 | 94.2 | 85/100 |
| *myosuroides* | 4 | 0.9 (75%) | 93.5 | 80/98.5 | 93.4 | 83.3/98.8 |
| | 3 | 0.6 (50%) | 84.2 | 73.3/97 | 83.6 | 61.7/96.3 |
| *Apera* | — | 1.2 (100%) | — | — | — | — |

TABLE-continued

Grass weed control results summarized across all countries by 0.6, 0.9 and 1.2 l/ha of Formulation Example 1 and Reference Formulation Example 14 in spring application in winter cereals in the efficacy tests (spring last assessment evaluation of control as % visual biomass reduction compared to untreated check, N = number of trials).

| | | | Mean % control at a range of doses of Formulation Example 1 and Reference Formulation Example 14 | | | |
|---|---|---|---|---|---|---|
| | | | Example 1 [%] | | Ref. Example 14 [%] | |
| Target | N | Dose rate l/ha (%) | Mean | Min/max | Mean | Min/max |
| spicaventi | 2 | 0.9 (75%) | 98 | 96.3/99.7 | 98.9 | 98/99.7 |
| | 2 | 0.6 (50%) | 93.2 | 91.7/94.7 | 91 | 86.7/95.3 |
| Avena fatua | 1 | 1.2 (100%) | 100 | 100/100 | 100 | 100/100 |
| | 5 | 0.9 (75%) | 96.3 | 90/100 | 97.3 | 95/100 |
| | 2 | 0.6 (50%) | 97 | 94/100 | 98.65 | 97.3/100 |
| Avena sp. | — | 1.2 (100%) | — | — | — | — |
| | 1 | 0.9 (75%) | 88.3 | 88.3/88.3 | 76.7 | 76.7/76.7 |
| | — | 0.6 (50%) | — | — | — | — |
| Avena sterilis | — | 1.2 (100%) | — | — | — | — |
| | 2 | 0.9 (75%) | 100 | 100/100 | 99.2 | 98.3/100 |
| | — | 0.6 (50%) | — | — | — | — |
| Lolium multiflorum | 4 | 1.2 (100%) | 90.8 | 65/100 | 93.9 | 64/100 |
| | 5 | 0.9 (75%) | 95.5 | 88.3/100 | 93.3 | 80/100 |
| | 3 | 0.6 (50%) | 87.2 | 68.3/100 | 87 | 80/100 |
| Lolium rigidum | 4 | 1.2 (100%) | 66.6 | 41.7/96.3 | 71.9 | 53.3/94.3 |
| | 1 | 0.9 (75%) | 97.3 | 97.3/97.3 | 96.7 | 96.7/96.7 |
| | — | 0.6 (50%) | — | — | — | — |
| Lolium sp. | 1 | 1.2 (100%) | 60 | 60/60 | 40 | 40/40 |
| | — | 0.9 (75%) | — | — | — | — |
| | — | 0.6 (50%) | — | — | — | — |
| Phalaris brachystachys | — | 1.2 (100%) | — | — | — | — |
| | 1 | 0.9 (75%) | 100 | 100/100 | 98.3 | 98.3/98.3 |
| | — | 0.6 (50%) | — | — | — | — |
| Phalaris paradoxa | — | 1.2 (100%) | — | — | — | — |
| | 4 | 0.9 (75%) | 97.3 | 90/100 | 99.8 | 99.3/100 |
| | — | 0.6 (50%) | — | — | — | — |
| Phalaris sp. | — | 1.2 (100%) | — | — | — | — |
| | 2 | 0.9 (75%) | 88.4 | 86.7/90 | 87.7 | 85.3/90 |
| | — | 0.6 (50%) | — | — | — | — |

The invention claimed is:
1. A mixture comprising:
2,2-dimethyl-propionic acid 8-(2,6-diethyl-4-methyl-phenyl)-9-oxo-1,2,4,5-tetrahydro-9H-pyrazolo[1,2-d][1,4,5]oxadiazepin-7-yl ester;
5-chloro-8-quinolyloxyacetic acid-1-methylhexylester;
a butanol PO/EO copolymer;
a condensation product of castor oil and ethyleneoxide;
a block copolymer of oxirane and methyloxirane;
a acrylic bead polymer based on isobutyl methacrylate;
tris(2-ethylhexyl) phosphate;
2-methyl-2,4-pentanediol; and
a mixture of heavy aromatic hydrocarbons.
2. The mixture of claim 1, wherein the isobutyl methacrylate polymer is present in from 0.5% to 7% by weight of the mixture.

3. The mixture of claim 1, wherein the kinematic viscosity of the mixture measured at 40° C., is 20.5 mm$^2$/second or more.

4. The mixture of claim 1, wherein 2methyl-2,4-pentanediol is present from 5% to 50% by weight of the mixture.

5. The mixture of claim 1, which is in the form of an emulsifiable concentrate (EC).

6. The mixture of claim 1, wherein 2,2-dimethyl-propionic acid 8-(2,6-diethyl-4-methyl-phenyl)-9-oxo-1,2,4,5-tetrahydro-9H-pyrazolo[1,2-d][1,4,5]oxadiazepin-7-yl ester is from 0.5% to 30% by weight of the mixture.

7. The mixture of claim 1, wherein the solvent system mixture does not comprise tetrahydrofurfuryl alcohol.

* * * * *